United States Patent
RamachandraRao et al.

(10) Patent No.: US 10,370,719 B2
(45) Date of Patent: Aug. 6, 2019

(54) METHOD AND DEVICE FOR DIAGNOSING ORGAN INJURY

(71) Applicants: Hitachi Chemical Co., Ltd., Tokyo (JP); Hitachi Chemical Co. America, Ltd., San Jose, CA (US); The Regents of the University of California, Oakland, CA (US)

(72) Inventors: Satish P. RamachandraRao, San Diego, CA (US); Ravindra Lall Mehta, La Jolla, CA (US); Masato Mitsuhashi, Irvine, CA (US); Taku Murakami, Irvine, CA (US)

(73) Assignees: Hitachi Chemical Co., Ltd., Tokyo (JP); Hitachi Chemical Co. America, Ltd., San Jose, CA (US); The Regents of the University of California, Oakland, CA (US)

( * ) Notice: Subject to any disclaimer, the term of this patent is extended or adjusted under 35 U.S.C. 154(b) by 89 days.

(21) Appl. No.: 15/526,296

(22) PCT Filed: Nov. 12, 2015

(86) PCT No.: PCT/US2015/060311
§ 371 (c)(1),
(2) Date: May 11, 2017

(87) PCT Pub. No.: WO2016/077537
PCT Pub. Date: May 19, 2016

(65) Prior Publication Data
US 2017/0335397 A1    Nov. 23, 2017

Related U.S. Application Data

(60) Provisional application No. 62/078,810, filed on Nov. 12, 2014.

(51) Int. Cl.
*C12Q 1/68* (2018.01)
*C12Q 1/6883* (2018.01)

(52) U.S. Cl.
CPC ...... *C12Q 1/6883* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | |
|---|---|---|
| 3,583,627 A | 6/1971 | Wilson |
| 4,895,706 A | 1/1990 | Root et al. |
| 4,925,572 A | 5/1990 | Pall |
| 5,139,685 A | 8/1992 | de Castro et al. |
| 5,372,945 A | 12/1994 | Alchas et al. |
| 5,647,990 A | 7/1997 | Vassarotti |
| 5,733,449 A | 3/1998 | Bowers et al. |
| 5,747,256 A | 5/1998 | Yan et al. |
| 6,329,179 B1 | 12/2001 | Kopreski |
| 6,375,855 B1 | 4/2002 | Vassarotti |
| 6,964,850 B2 | 11/2005 | Bevilacqua et al. |
| 7,026,121 B1 | 4/2006 | Wohlgemuth et al. |
| 7,741,023 B2 | 6/2010 | Mitsuhashi |
| 7,745,180 B2 | 6/2010 | Mitsuhashi |
| 8,567,609 B2 | 10/2013 | Landrigan et al. |
| 8,591,391 B2 | 11/2013 | Chavarria et al. |
| 9,012,615 B2 | 4/2015 | Mitsuhashi et al. |
| 9,458,496 B2 | 10/2016 | Mitsuhashi et al. |
| 9,662,649 B2 | 3/2017 | Mitsuhashi et al. |
| 9,719,129 B2 | 8/2017 | Mitsuhashi et al. |
| 9,790,542 B2 | 10/2017 | Mitsuhashi et al. |
| 2002/0011450 A1 | 1/2002 | Kelly et al. |
| 2003/0203453 A1 | 10/2003 | Leonard |
| 2004/0029124 A1 | 2/2004 | Zohlnhofer et al. |
| 2004/0072193 A1 | 4/2004 | Mitsuhashi |
| 2004/0203037 A1 | 10/2004 | Lo et al. |
| 2004/0258570 A1 | 12/2004 | Beebe et al. |
| 2004/0265864 A1 | 12/2004 | Mitsuhashi |

(Continued)

FOREIGN PATENT DOCUMENTS

| | | | |
|---|---|---|---|
| EP | 0588564 A1 * | 3/1994 | ............ B01D 15/00 |
| JP | 1997-067336 | 3/1997 | |
| JP | 2013-514090 | 4/2013 | |
| WO | WO 1993/19831 | 10/1993 | |
| WO | WO 2002/057414 | 7/2002 | |
| WO | WO 2006/045053 | 4/2006 | |
| WO | WO 2008/092993 | 8/2008 | |
| WO | WO 2009/015357 | 1/2009 | |
| WO | WO 2009/057695 | 5/2009 | |
| WO | WO 2009/070442 | 6/2009 | |
| WO | WO 2009/100029 | 8/2009 | |
| WO | WO 2010/056337 | 5/2010 | |
| WO | WO 2010/086163 | 8/2010 | |

(Continued)

OTHER PUBLICATIONS

Rahman et al. American Family Physician 86 (7) 2012, 631-639. (Year: 2012).*

(Continued)

*Primary Examiner* — Jeffrey S Lundgren
*Assistant Examiner* — Michael J Schmitt
(74) *Attorney, Agent, or Firm* — Knobbe Martens Olson & Bear LLP

(57) ABSTRACT

The present disclosure relates to methods of collecting exosomes and microvesicles (EMV) from urine and isolating corresponding mRNA in order to diagnose and treat acute kidney injury (AKI). In particular, certain embodiments relate to the method of capturing EMV from urine applied to a filter device that is capable of capturing EMV. Nucleic acids such as mRNA can be isolated from the EMV using an oligo(dT)-coated plate designed to accommodate the filter device and then used for further molecular analysis. Quantification of the collected nucleic acids may then be used in the diagnosis and/or treatment of IBD.

13 Claims, 26 Drawing Sheets

(56) References Cited

U.S. PATENT DOCUMENTS

| | | | |
|---|---|---|---|
| 2006/0008804 A1* | 1/2006 | Chibout | C12Q 1/6883 435/6.14 |
| 2006/0144790 A1 | 7/2006 | Kelly et al. | |
| 2007/0254351 A1 | 11/2007 | Abrignani et al. | |
| 2007/0264272 A1 | 11/2007 | Perreault et al. | |
| 2008/0009009 A1 | 1/2008 | Mitsuhashi | |
| 2008/0015162 A1 | 1/2008 | Bhanot et al. | |
| 2008/0025967 A1 | 1/2008 | Doi et al. | |
| 2008/0188816 A1 | 8/2008 | Shimazaki et al. | |
| 2008/0233573 A1 | 9/2008 | Storm et al. | |
| 2008/0268429 A1 | 10/2008 | Pietrzkowski | |
| 2009/0011410 A1 | 1/2009 | Mitsuhashi | |
| 2009/0023149 A1 | 1/2009 | Knudsen | |
| 2009/0149333 A1 | 6/2009 | Knudsen et al. | |
| 2009/0258379 A1 | 10/2009 | Klein et al. | |
| 2010/0113290 A1 | 5/2010 | Klass et al. | |
| 2010/0196426 A1 | 8/2010 | Skog | |
| 2010/0203529 A1 | 8/2010 | Kuslich et al. | |
| 2011/0195426 A1 | 8/2011 | Russo | |
| 2011/0223583 A1 | 9/2011 | Gordon et al. | |
| 2011/0287964 A1* | 11/2011 | Bonventre | G01N 33/6893 506/9 |
| 2012/0211566 A1 | 8/2012 | Hensel et al. | |
| 2012/0264628 A1 | 10/2012 | Okamoto et al. | |
| 2013/0089864 A1* | 4/2013 | Mitsuhashi | C12Q 1/6809 435/6.11 |
| 2013/0165338 A1* | 6/2013 | Schmidt-Ott | C12Q 1/6883 506/9 |
| 2013/0172208 A1 | 7/2013 | Mitsuhashi | |
| 2013/0337462 A1 | 12/2013 | Mergemeier | |
| 2014/0148348 A1 | 5/2014 | Kuslich | |
| 2014/0148350 A1 | 5/2014 | Spetzler | |
| 2014/0194613 A1 | 7/2014 | Skog et al. | |
| 2015/0275301 A1 | 10/2015 | Mitsuhashi et al. | |
| 2016/0122823 A1 | 5/2016 | Mitsuhashi | |
| 2016/0222456 A1 | 8/2016 | Yamamoto | |
| 2017/0184575 A1 | 6/2017 | Murakami | |

FOREIGN PATENT DOCUMENTS

| | | | |
|---|---|---|---|
| WO | WO 2011/031892 | 3/2011 | |
| WO | WO 2011/100458 | 8/2011 | |
| WO | WO 2011/127219 | 10/2011 | |
| WO | WO 2011/156734 | 12/2011 | |
| WO | WO 2011/156763 | 12/2011 | |
| WO | WO-2011156763 A1* | 12/2011 | C12Q 1/6809 |
| WO | WO 2012/102963 | 8/2012 | |
| WO | WO-2012102963 A1* | 8/2012 | G01N 33/6893 |
| WO | WO 2013/028788 | 2/2013 | |
| WO | WO 2013/041913 | 3/2013 | |
| WO | WO 2013/043922 | 3/2013 | |
| WO | WO 2013/134786 | 9/2013 | |
| WO | WO 2013/188846 | 12/2013 | |
| WO | WO 2014/055687 | 4/2014 | |
| WO | WO 2014/182330 | 11/2014 | |
| WO | WO 2015/050891 | 4/2015 | |
| WO | WO 2015/082372 | 6/2015 | |
| WO | WO 2016/077537 | 5/2016 | |
| WO | WO 2017/040515 | 3/2017 | |
| WO | WO 2017/040520 | 3/2017 | |

OTHER PUBLICATIONS

Kim et al. Molecular Cancer 2010, 9:3. (Year: 2010).*
"Binding Assays with Membranes," Jan. 1, 2006, Protein Biochemistry and Protoeomics, Elsevier, pp. 37-39.
Absolute Quantitation Using Standard Curve Getting Guide, Applied Biosystems, pp. i-viii and 1-80, Jun. 2010, printed from http://www3.appliedbiosystems.com/cms/groups/mcb_support/documents/generaldocuments/cms_032176.pdf.
Akoglu et al.: "Interleukin-2 in CD8+ T cells correlates with Banff score during organ rejectionin liver transplant recipients," Clin Exp Med (2009) 9:259-262.

Alvarez ML, et al., Comparison of protein, microRNA, and mRNA yields using different methods of urinary exosome isolation for the discovery of kidney disease biomarkers. Kidney Int. 82: 1024-1032, 2012.
Anders S, et al., Count-based differential expression analysis of RNA sequencing data using R and Bioconductor. Nat. Protoc. 8: 1765-1786, 2013.
Anglicheau et al., "Discovery and Validation of a Molecular Signature for the Noninvasive Diagnosis of Human Renal Allograft Fibrosis," NIH Public Access, Author Manuscript, Transplantation Jun. 15, 2012; 93(11): 1136-1146.
Arteaga et al., Endothelial microparticles and platelet and leukocyte activation in patients with the metabolic syndrome, Am J Cardiol, vol. 98:70-74 (2006).
Bachmann et al., Renal effects of Tamm-Horsfall protein (uromodulin) deficiency in mice, Am J Physiol, Renal Physiol, 288:F559-567 (2005).
Baldi P, et al., A Bayesian framework for the analysis of microarray expression data: regularized t-test and statistical inferences of gene changes. Bioinformatics 17: 509-519, 200.
Bakris, GL., Recognition, pathogenesis, and treatment of different stages of nephropathy in patients with type 2 diabetes mellitus. Mayo Clinic Proceedings, vol. 86, No. 5, pp. 444-456, May 2011.
Barnett et al., Angiotensin-Receptor Blockade versus Converting-Enzyme Inhibition in Type 2 Diabetes and Nephropathy, N Eng J Med (2004) 351:1952-61.
Beltrami, et al.: "Analysis of urinary microRNAs in chronic kidney disease: Figure1," Biochemical Society Transactions, vol. 12, No. 0. 4, Aug. 1, 2012, pp. 4-879.
Bio Scientific, "ExoMir Kit Manual", Catalog 5145, www.yumpu.com/en/document/view/30138118/exomirtm-kit-manual-nordic-biosite/2, Feb. 17, 2015.
Botteman MF, et al., The health economics of bladder cancer: a comprehensive review of the published literature. PharmacoEconomics 21: 1315-1330, 2003.
Brush M, et al., Glomerular Autoimmune Multicomponents of Human Lupus Nephritis In Vivo: α-Enolase and Annexin AI. J. Am. Soc. Nephrol. 25: 2483-2498, 2014.
The Cancer Genome Atlas Research Network: Comprehensive molecular characterization of urothelial bladder carcinoma. Nature [Internet] advance online publication: 2014 Available from: http://www.nature.com/nature/journal/vaop/ncurrent/full/nature12965.html [cited Feb. 21, 2014].
Chapter 6: Transplantation, 2014 USRDS Annual Data Report, vol. 2 ESRD, pp. 153-162.
Chen et al., Microfluidic isolation and transcriptome analysis of serum microvesicles, J Royal Soc of Chem (2010) vol. 10:505-511.
Chen et al., Inhibition of Ultraviolet B-Induced c-fos Gene Expression and p38 Mitogen-Activated Protein Kinase Activation by (−)-Epigallocatechin Gallate in a Human Keratinocy1e Cell Line, Molecular Carcinogenesis (1999) vol. 24(2):79-84.
Cheruvanky et al.: Rapid isolation of urinary exosomal biomarkers using a namomembrane ultrafiltration concentrator, Am J. Physio. Renal. Physiol 292: F1657-F1661, 2007.
Common Cancer Types [Internet]. Natl. Cancer Inst. Available from: http://www.cancer.gov/types/common-cancers [cited Aug. 6, 2015].
Conde-Vancells et al., Candidate biomarkers in exosome-like vesicles purified from rat and mouse urine samples, Proteomics Clin Appl 4(4):416-25 (2010).
Cutillas et al., The urinary proteome in Fanconi syndrome implies specificity in the reabsorption of proteins by renal proximal tubule cells, Am J Physio Renal Physiol (2004) vol. 287(3):353-364.
Dennis et al., Identification from public data of molecular markers of adenocarcinoma characteristic of the site of origin, Cancer Res, vol. 62(21):5999-6005 (2002).
Duffield et al. Simultaneous determination of multiple mRNA levels utilizing MALDI-TOF mass spectrometry and biotinylted dideoxynucleotides. RNA, vol. 16, pp. 1285-1291, (2010).
Enard et al., Intra- and Interspecific Variation in Primate Gene Expression Patterns, Science (2002) vol. 296:340.

(56) References Cited

OTHER PUBLICATIONS

Erusalimsky et al.: A Glass Fiber/Diethylaminoethyl Double Filter Binding Assay That Measures Apoptotic Internucleosomal DNA Fragmentation, Analytical Biochemistry 242, 187-196 (1996) Article No. 0452.

Ferguson et al.: Vesicular Localization and Activity-Dependent Trafficking of Presynaptic Choline Transponders, The Journal of Neuroscience, Oct. 29, 2003, 23(30):9697-9699.

Fuchs et al., "An Exploratory Evaluation of the Utility of Transcriptional and Urinary Kidney Injury Biomarkers for the Prediction of Aristolochic Acid-Induced Renal Injury in Male Rates," Veterinary Pathology, 2014, vol. 51 (3) 680-694.

Gallagher et al. "Unit 10.8: Immunoblotting and Immunodetection" in Current Protocols in Molecular Biology, Supplement 66, pp. 10.8.1-10.8.24, (2004).

Gene Cards DEFA3 Gene, first internet archive Aug. 7, 2010, pp. 1-14.

Golub, et al.: "Molecular Classification of Cancer: Class Discovery and Class Prediction by Gene Expression Monitoring," Science, vol. 286, pp. 531-537, Oct. 1999.

Gonzales et al., Chapter 6: Isolation and Purification of Exosomes in Urine in Alex J. Rai (ed.), The Urinary Proteome: Methods and Protocols, Methods in Molecular Biology, vol. 641, pp. 89-99, 2010.

Gonzales et al., Large-scale proteomics and phosphoproteomics of urinary exosomes, J Am Soc Nephrol, 20(2):363-79 (2009).

Grams et al.: "Fluid Balance, Diuretic Use, and Mortality in Acute Kidney Injury," Clin J AM Soc Nephrol 6:966-973, Mar. 10, 2011.

Grant et al., A filtration-based protocol to isolate human plasma membrane-derived vesicles and exosomes from blood plasma. Journal of Immunocological Methods, vol. 371, pp. 143-151, Jun. 30, 2011.

Guo et al., Surfactant protein gene A, B, and D marker alleles in chronic obstructive pulmonary disease of a Mexican population, Eur Respir J, 18(3):482-90 (2001).

Haas et al., Patient characteristics associated with successful mobilizing and autografting of peripheral blood progenitor cells in malignant lymphoma, Blood (1994) vol. 83(12):3787-3794.

Harada and Mitsuhashi, "Assessment of post-transplant kidney function by measuring glomerulus and tubule specific mRNAs in urine exosome," American Journal of Transplantation, vol. 12, Supp. 3, pp. 369-370, Abstract No. 1158, May 2012.

Hashem, Biochemical and expression studies on Acquaporin 9 (AQP9) in wild and AQP9 knockout mice, Veterinarski Archiv (2010) vol. 80(1):93-112.

Hess et al., The hydroxylamine of sulfamethoxazole synergizes with FK506 and cyclosporin A, inhibiting T-Cell proliferation, J Pharm & Exp Tech (1996) vol. 281(1):540-548.

Hewitt et al., Discovery of Protein Biomarkers for Renal Diseases, J Am Soc Nephrol (2004) vol. 15(7):1677-1689.

Hoorn et al., Prospects for urinary proteomics: exosomes as a source of urinary biomarkers, Nephrology, 10:283-290 (2005).

Hornbeck, et al., "Unit 11.2: Enzyme-Linked Immunosorbent Assays (ELISA)" in Current Protocols in Biology, Supplement 15, pp. 11.2.1-11.2.22, (1991).

Hotfilder et al., Def-2, -3, -6 and -8, novel mouse genes differentially expressed in the haemopoietic system, Brit J Haematol (1999) vol. 106:335-344.

Hunter et al., Detection of microRNA expression in human peripheral blood microvesicles, PLoS One 3:e3694 (2008).

Ide et al., "Transduction of Murine Hematopoietic Stem Cells and In Vivo Selection of Gene-Modified Cells," Methods in Molecular Biology, vol. 433,: vol. 1: Production and In Vivo Applications of Gene Transfer Vectors, 2008, pp. 213-228.

Ito et al., Myeloid Reconstruction. Serum stem cell growth factor for monitoring hematopoietic recovery following stem cell transplantation, Bone Marrow Transplantation (2003) vol. 32:391-398.

Jimenez et al., Endothelial microparticles released in thrombotic thrombocytopenic purpura express von Willibrand factor and markers of endothelial activation, Br J Haemat (2003) vol. 123(5):896-902.

Keller et al., "Body fluid derived exosomes as a novel template for clinical diagnostics," Journal of Translational Medicine, vol. 9, 86, Jun. 2011, printed as pp. 1/9-9/9.

Klein et al., Ex-Vivo Assessment of Candidate Anti-Inflammatory Agents in the Treatment of Gram Negative Sepsis, Immun & Infec Dis (1994) vol. 4(1):33-35.

Koga et al., Purification, characterization and biological significance of tumor-derived exosomes, Anticancer Res, 25(6A):3703-7 (2005).

Labsource: Whatman Glass Microfiber Filters, printed from internet Dec. 12, 2009 2011:<URL:http://www.labsource.com/Catalog/Group.aspx?GroupID=82>] p. 1.

Lescuyer et al., Proteomics: Clinical Applications (2008) vol. 2(7-8):1008.

Liu et al., Transcriptome profiling and sequencing of differentiated human hematopoietic stem cells reveal lineage-specific expression and alternative splicing of genes, Physiol Genomics 43:1117-1134, 2011.

Lu et al., "Tracking single hematopoietic stem cells in vivo using high-throughput sequencing in conjunction with viral genetic barcoding," Nature Biotechnology 29, 928-933 (2011) and supplementary data.

Lucendo et al., Treatment with topical steroids downregulates IL-5, eotaxin-1/CCL11, and eotaxin-3/CCL26 gene expression in eosinophilic esophagitis, Am J Gastro 103(9):2184-93 (2008).

Luo et al., RANTES stimulates inflammatory cascades and receptor modulation in murine astrocytes, 39(1):19-30 (2002).

Masyuk, et al.: "Exosomes in the pathogenesis, diagnostics and therapeutics of liver diseases," Journal of Hepatology 2013 vol. 59, 621-625.

Mathivanan, et al.: "ExoCarta 2012: database of exosomal proteins, RNA and lipids," Nucleic Acids Research, vol. 40, No. D1, Oct. 11, 2011, pp. D1241-D1244.

Mathivanan, et al.: "Exosomes: Extracellular Organelles Important in Intercellular Communication," J of Proteomics 73(10)1907-20, 2010.

Melé M, et al., The human transcriptome across tissues and individuals. Science 348: 660-665, 2015.

Mi H, et al., Large-scale gene function analysis with the PANTHER classification system. Nat. Protoc. 8: 1551-1566, 2013.

Millàn, et al.: "Intracellular IFN-Y and IL-2 expression monitoring as surrogate markers of the risk of acute rejection and personal drug response in de novo liver transplant recipients," Cytokine 61 (2013) 556-564.

Miranda et al., Nucleic acids within urinary exosomes/microvesicles are potential biomarkers for renal disease, Kidney Intl (2010) vol. 78(2):191-199.

Mitchell et al., Can urinary exosomes act as treatment response markers in prostate cancer? J Transl Med, 12:7:4 (2009).

Mitsuhashi et al., Quantification of mRNA in Whole Blood by Assessing Recovery of RNA and Efficiency of cDNA Synthesis, Clin Chem (2006) vol. 52(4):634-642.

Mitsuhashi, Ex vivo simulation of leukocyte function: Stimulation of specific subset of leukocytes in whole blood followed by the measurement of function-associated nRNAs, J Immun Meth (2010) vol. 363(1):95-100.

Muller, Gunter: "Microvesicles/exosomes as potential novel biomarkers of metabolic diseases," Diabetes, Metabolic Syndrom and Obesity: Targets and Therapy, Aug. 1, 2012, p. 247.

Murakami et al.: "Development of Glomerulus-, Tubuel-, and Collecting Duct-Specific mRNA Assay in Human Urinary Exosomes and Microvesicles," PLOS One vol. 9, Oct. 2014, pp. 1-10.

Nilsson et al., Prostate cancer-derived urine exosomes: a novel approach to biomarkers for prostate cancer, Br J Cancer 100:1603-1607 (2009).

Notterman et al., in Microarrays and Cancer Research (2002) Warrington et al. (eds.) pp. 81-111 at pp. 81-82.

Olszewska-Pazdrak et al., Cell-specific expression of RANTES, MCP-1, and MIP-1 alpha by lower airway epithelial cells and eosinophils infected with respiratory syncytial virus, J Virol, 72(6):4756-64 (1998).

(56) References Cited

OTHER PUBLICATIONS

OPTN: Organ Procurement and Transplantation Network—OPTN [Internet]. 2015 Available from: http://optn.transplant.hrsa.gov/ [cited Jun. 27, 2015].
Patterson, SD. "Unit 10.22: Protein Identification and Characterization by Mass Spectrometry" in Current Protocols in Molecular Biology, Supplement 41, pp. 10.22.1-10.22.24, (1998).
Peake et al., "A comparison of the ability of levels of urinary biomarker proteins and exosomal mRNA to predict outcomes after renal transplantation," PLoS One, Jun. 11, 2014, vol. 9, No. 2, e98644, pp. 1-7.
Perez A, et al., A Pilot Study on the Potential of RNA-Associated to Urinary Vesicles as a Suitable Non-Invasive Source for Diagnostic Purposes in Bladder Cancer. Cancers 6: 179-192, 2014.
Pisitkun et al., Discovery of urinary biomarkers, Mol Cell Proteomics, 5(10):1760-71 (2006).
Pisitkun et al., Identification and proteomic profiling of exosomes in human urine, Proc Natl Acad Sci USA, 101:13368-73 (2004).
Pisitkun et al., "Application of systems biology principles to protein biomarker discovery: urinary exosomal proteome in renal transplantation," Proteomics Clin Appl, Jun. 29, 2012, vol. 6, No. 5-6, pp. 268-278.
Post et al., Demonstration of the presence of independent pre-osteoblastic and pre-adipocytic cell populations in bone marrow-derived mesenchymal stem cells, Bone, 43(1):32-9 (2008).
Properzi F, et al., Exosomes: the future of biomarkers in medicine. Biomark. Med. 7: 769-778, 2013.
Pusztai et al.: "Clinical trial design for microarray predictive marker discovery and assessment," Annals of Oncology 15: 1731-1737, 2004.
R Core Team: R: The R Project for Statistical Computing [Internet]. R Lang. Environ. Stat. Comput. R Found. Stat. Comput. Vienna Austria. Available from: http://www.r-project.org/ [cited Jun. 15, 2015].
Rappa et al., The stem cell-associated antigen CD133 (Prominin-1) is a molecular therapeutic target for metastatic melanoma, Stem Cells, 26:3008-17 (2008).
Rehm, Hubert: "Binding Assays with Membranes", 2.2 Binding, Protein Biochemistry and Proteomics, Elsevier, pp. 37-39.
Reeve J, et al., Molecular Diagnosis of T Cell-Mediated Rejection in Human Kidney Transplant Biopsies. Am. J. Transplant. 13: 645-655, 2012.
Roedder S, et al., The kSORT Assay to Detect Renal Transplant Patients at High Risk for Acute Rejection: Results of the Multicenter AART Study. PLoS Med 11: e1001759, 2014.
Sartorius Stedim Biotech., Ultrafiltration & Protein Purification Products. Fisher Scientic, pp. 1-96, Mar. 2011.
Sellam et al., Increased levels of circulating microparticles in primary Sjögren's syndrome, systemic lupus erythematosus and rheumatoid arthritis and relation with disease activity, Arthritis Res Ther 11(5):R156 (2009).
Sellarés J, et al., Molecular Diagnosis of Antibody-Mediated Rejection in Human Kidney Transplants. Am. J. Transplant. 13: 971-983, 2012.
Simpson et al., Proteomic profiling of exosomes: current perspectives, Proteomics 8(19):4083-99 (2008).
Sing T, et al., ROCR: visualizing classifier performance in R. Bioinformatics 21: 3940-3941, 2005.
Smalley et al., Isolation and identification of potential urinary microparticle biomarkers of bladder cancer, J Proteome Res 7:2088-96 (2008).
Smith ZL, et al., Urinary markers for bladder cancer. F1000Prime Rep. [Internet] 5: 2013 Available from: http://www.ncbi.nlm.nih.gov/pmc/articles/PMC3702217/ [cited Aug. 17, 2015].
Stahlberg et al., Properties of the reverse transcription reaction in mRNA quantification. Clinical Chemistry, vol. 50, No. 3, pp. 509-515, 2004.
Strausberg et al., Reading the Molecular Signatures of Cancer, Microarrays & Cancer Res (2002) pp. xi-xvi.

Suthanthiran M, et al., Urinary-Cell mRNA Profile and Acute Cellular Rejection in Kidney Allografts. N. Engl. J. Med. 369: 20-31, 2013.
Taub et al., Role of biomarkers in the diagnosis and prognosis of acute kidney injury in patients with cardiorenal sydrome, Expert Review of Cardiovascular Therapy, vol. 10, No. 5, pp. 657-667, May 1, 2012.
Taylor et al., MicroRNA signatures of tumor-derived exosomes as diagnostic biomarkers of ovarian cancer, Gynecol Oncol 110(1):13-21 (2008).
Théry et al., Isolation and characterization of exosomes from cell culture supernatants and biological fluids, Chapter 3, Curr Protoc Cell Biol, Unit 3.22 (2006).
Théry C, et al., Membrane vesicles as conveyors of immune responses. Nat. Rev. Immunol. 9: 581-593, 2009.
Théry C, et al., Exosomes: composition, biogenesis and function. Nat. Rev. Immunol. 2: 569-579, 2002.
Tockman et al., Considerations in bringing a cancer biomarker to clinical application, Cancer Res 1:52(9Suppl):2711s-2718s (1992).
Tomblyn et al., Guidelines for preventing infectious complications among hematopoietic cell transplantation recipients: A global perspective, Biol Blood Marrow Trans (2009) vol. 15:1143-1238.
Umeshita et al.: "Determination of the Presence of Interleukin-6 in Bile After Orthotopic Liver Transplantation," Annals of Surgery, vol. 223, No. 2, 204-211. 1996.
Vaes et al., Comprehensive microarray analysis of bone morphogenetic protein 2-induced osteoblast differentiation resulting in the identification of novel markers for bone development, J Bone Miner Res 17(12):2106-18 (2002).
Van Niel et al., Exosomes: a common pathway for a specialized function, J Biochem 140(1):13-21 (2006).
Van't Veer et al., Enabling personalized cancer medicine through analysis of gene-expression patterns, Nature 452(7187):564-70 (2008).
Vaidya, et al., Biomarkers of acute kidney injury, Annual Review of Pharmacology and Toxicology, Annual Review Inc., vol. 48, pp. 463-493, Feb. 1, 2008.
Waikar et al., Diagnosis, Epidemiology and Outcomes of Acute Kidney Injury, Clinical Journal of the American Society of Nephrology, vol. 3, No. 3, pp. 844-861, Feb. 20, 2008.
Wakabayashi, Therapeutic Research, 2001, vol. 22, No. 11, p. 2433-2437.
Warlé et al.: "Early Differentiation Between Rejection and Infection in Liver Transplant Patients by Serum and Biliary Cytokine Patterns," Transplantation, vol. 75, 146-151, No. 1, Jan. 15, 2003.
Wellmann et al., Detection of differentially expressed genes in lymphomas using cDNA arrays: identification of clustering as a new diagnostic marker for anaplastic large-cell lymphomas, Blood (2000) vol. 96(2):398-404.
Whitehead et al., Variation in tissue-specific gene expression among natural populations, Genome Biol 6(2):R13 (2005).
Xu et al., Gene expression in peripheral blood differs after cardioembolic compared with large—vessel atherosclerotic stroke: biomarkers for the etiology of ischemic stroke, JCBFM (2008) vol. 28:1320-1328.
Yuan Y, et al., Urinary candidate biomarker discovery in a rat unilateral ureteral obstruction model. Sci. Rep.
Zefon International. Glass Fiber Filters, Jan. 14, 2010 (printed from internet Oct. 7, 2011) <http://web.archive.org/web/20100114112921/http://www.zefon.com/store/glass-fiber-filters/>].
Zheng et al., Urinary Podocyte-Associated mRNA profile in Various Stages of Diabetic Nephropathy, PLOS one (2011) vol. 6(5):1-7.
Zhou et al., Urinary exosomal transcription factors, a new class of biomarkers for renal disease, Kidney Intl (2008) vol. 74(5):613-621.
Zhou et al., Exosomal Fetuin-A identified by proteomics: A novel urinary biomarker for detecting acute kidney injury, Kidney International, Nature Publishing Group, vol. 70, No. 10, Nov. 1, 2006, pp. 1847-1857.
Zhou et al., Acute Kidney Injury Biomarkers—Needs, Present Status, and Future Promise. Dec. 17, 2008. www.ncbi.nlm.nih.gov/pmc/articles/PMC2603572/pdf/nihms42415.pdf.
Zucker et al., Immature platelet fraction as a predictor of platelet recovery following hematopoietic progenitor cell transplantation, Lab Hematol (2006) vol. 12:125-130.

(56) References Cited

OTHER PUBLICATIONS

Fang DY, et al., Exosomes and the kidney: Blaming the messenger. Nephrology 18: 1-10, 2013.

Ka S-M, et al., Urine Annexin A1 as an Index for Glomerular Injury in Patients. Dis. Markers.

Apr. 4, 2016 ISR/WO from related PCT App No. PCT/US2015/60311.

May 16, 2017 International Preliminary Report on Patentability from related PCT App No. PCT/US2015/60311.

Feb. 28, 2018 European Supplemental Search Report re related App No. PCT/US2015/60311.

* cited by examiner

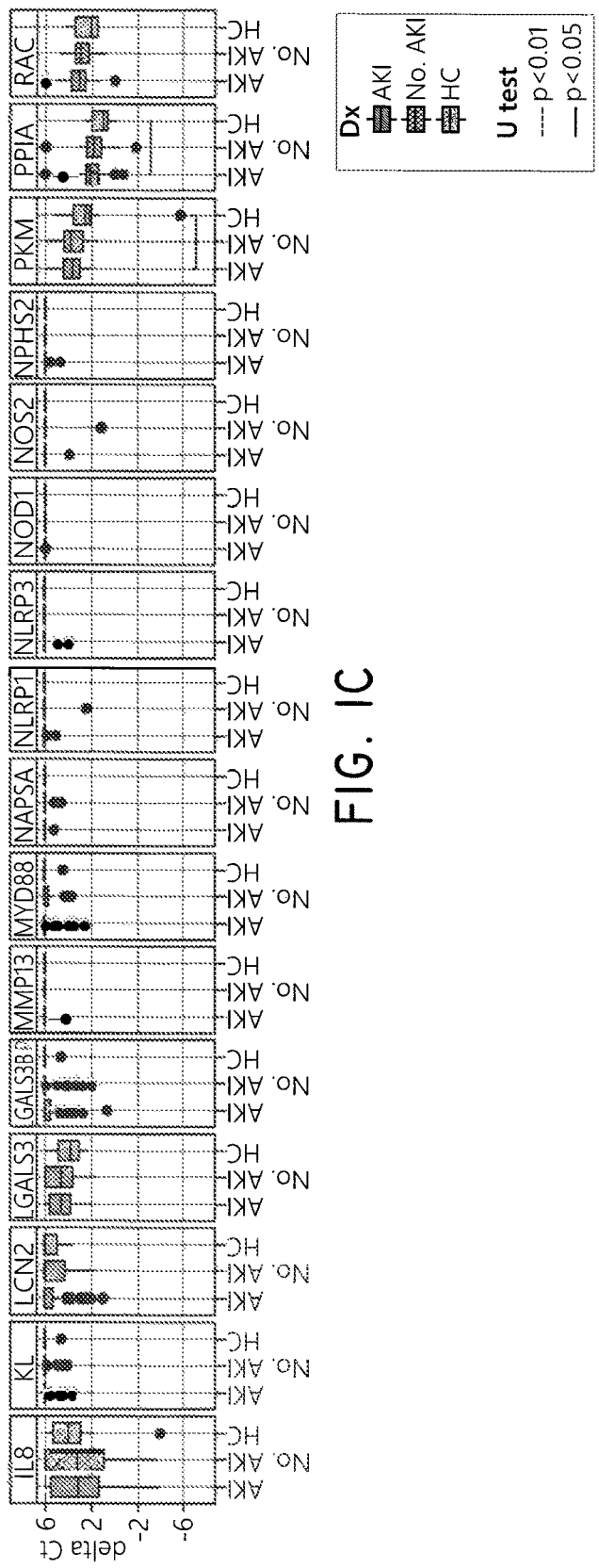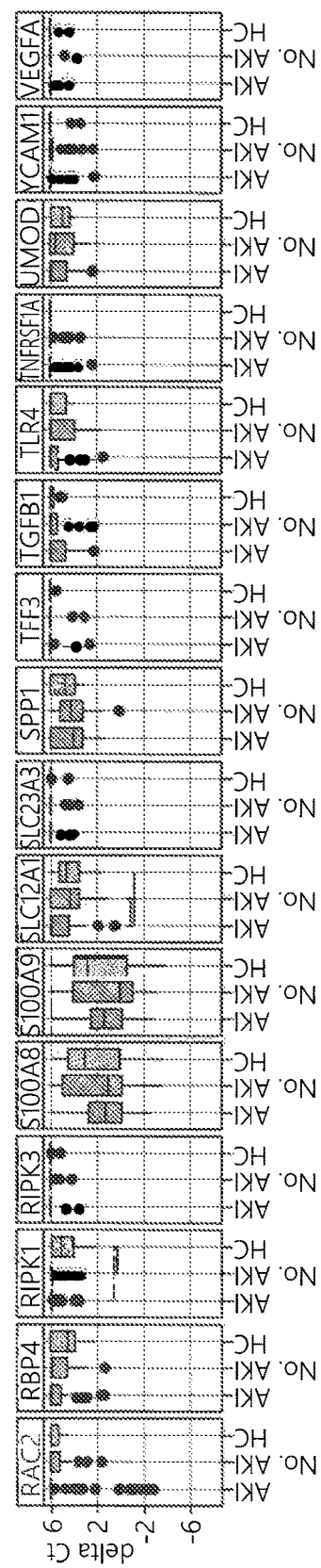
FIG. 1C
FIG. 1D

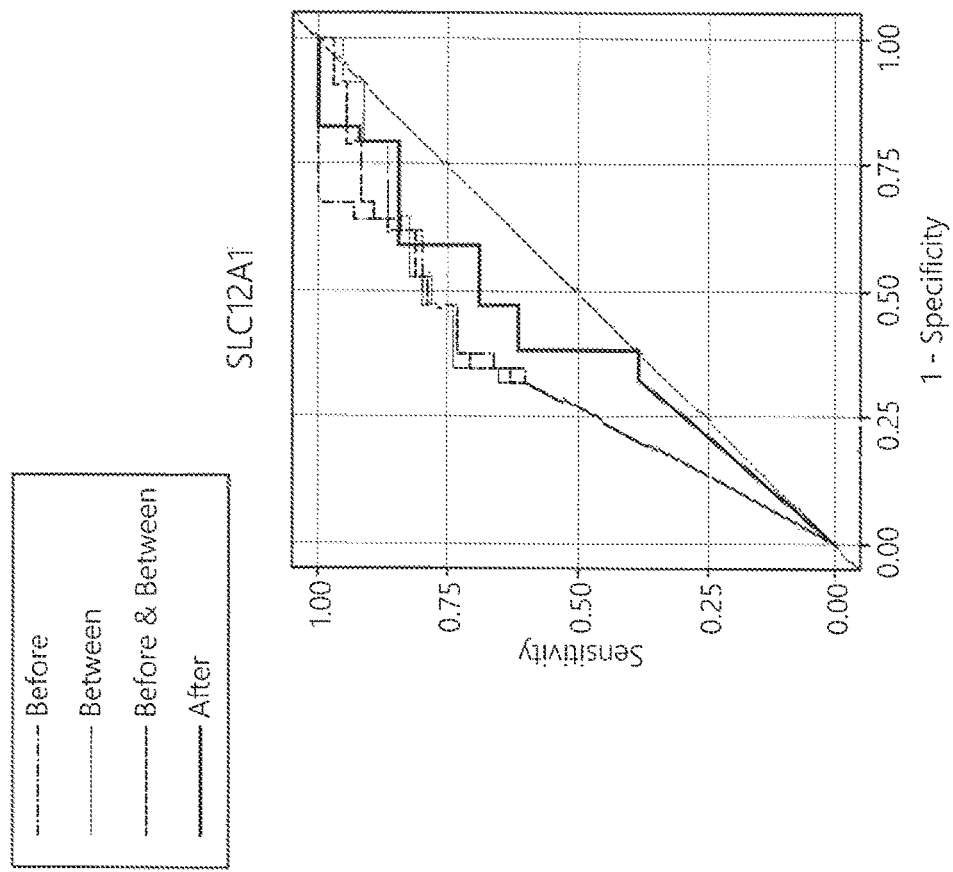
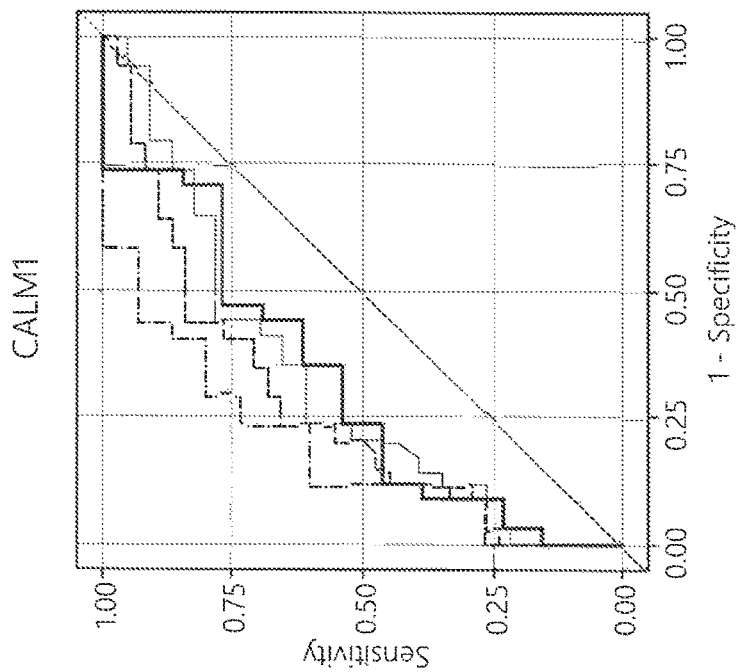
FIG. 2A
FIG. 2B

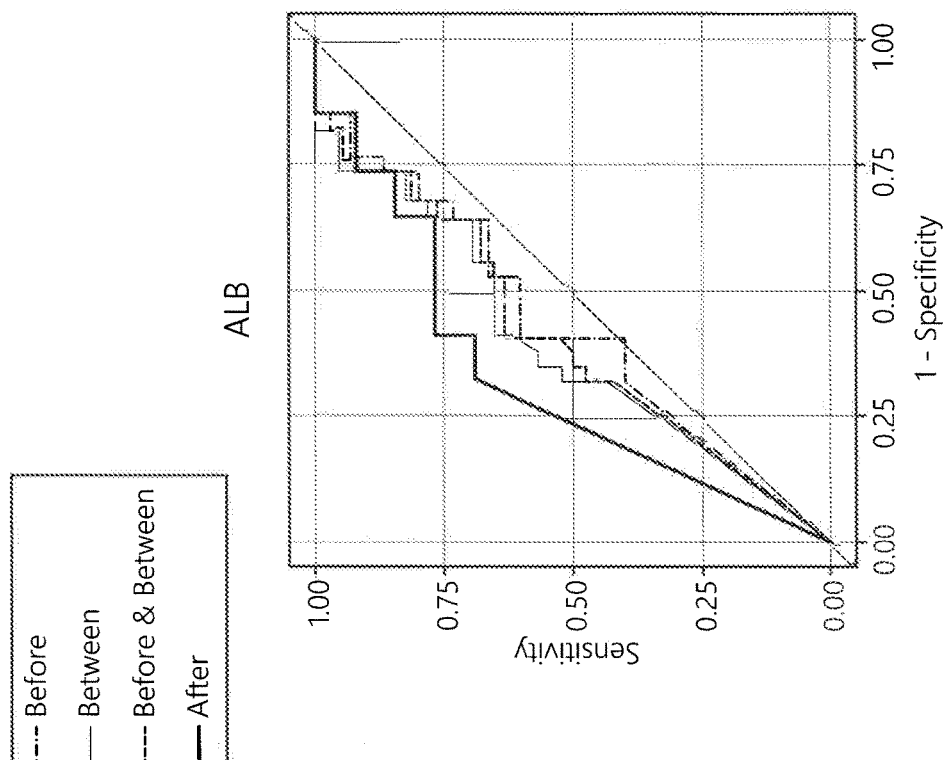
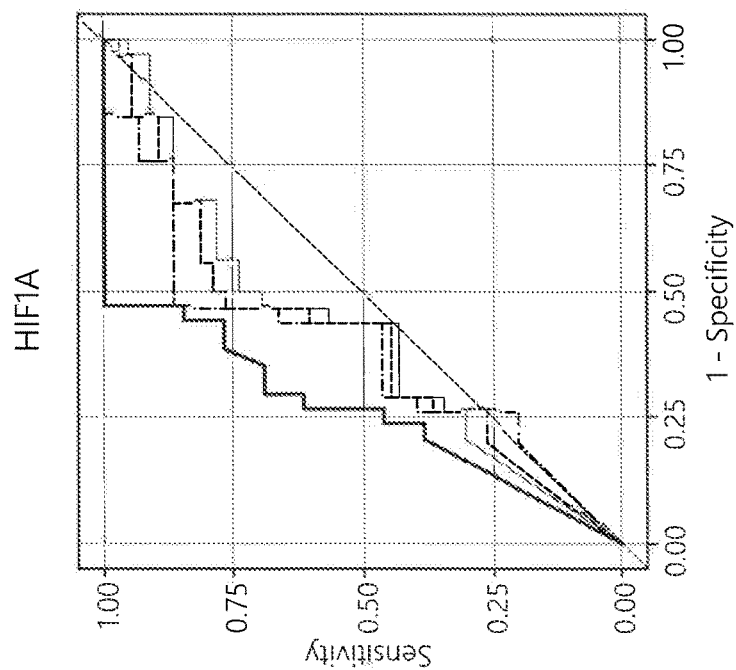
FIG. 2E
FIG. 2F

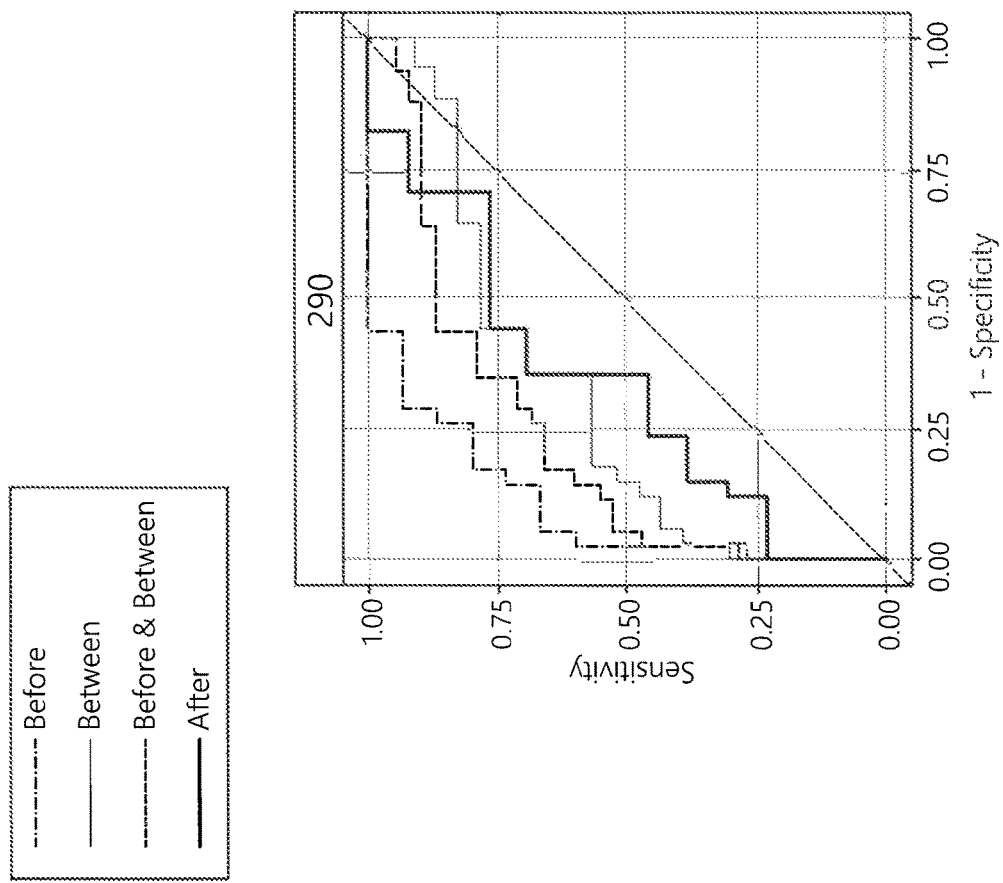
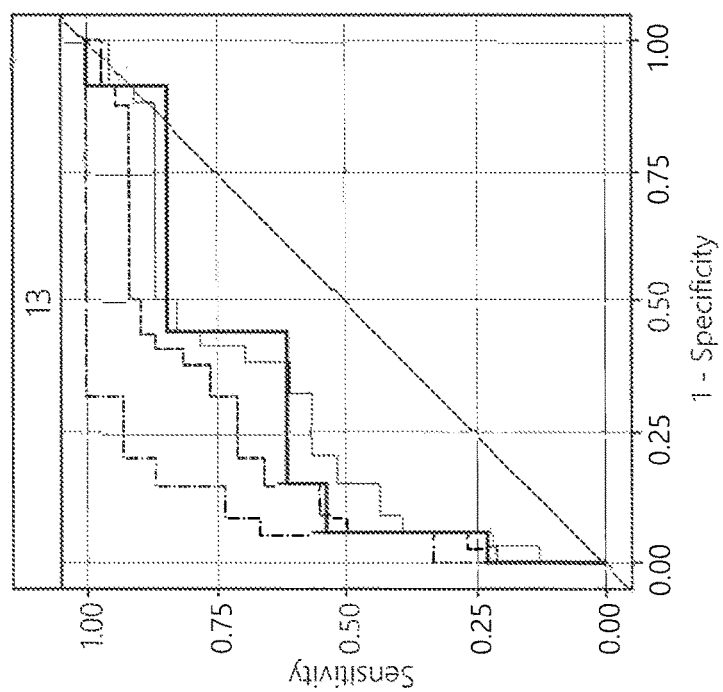
FIG. 3A
FIG. 3B

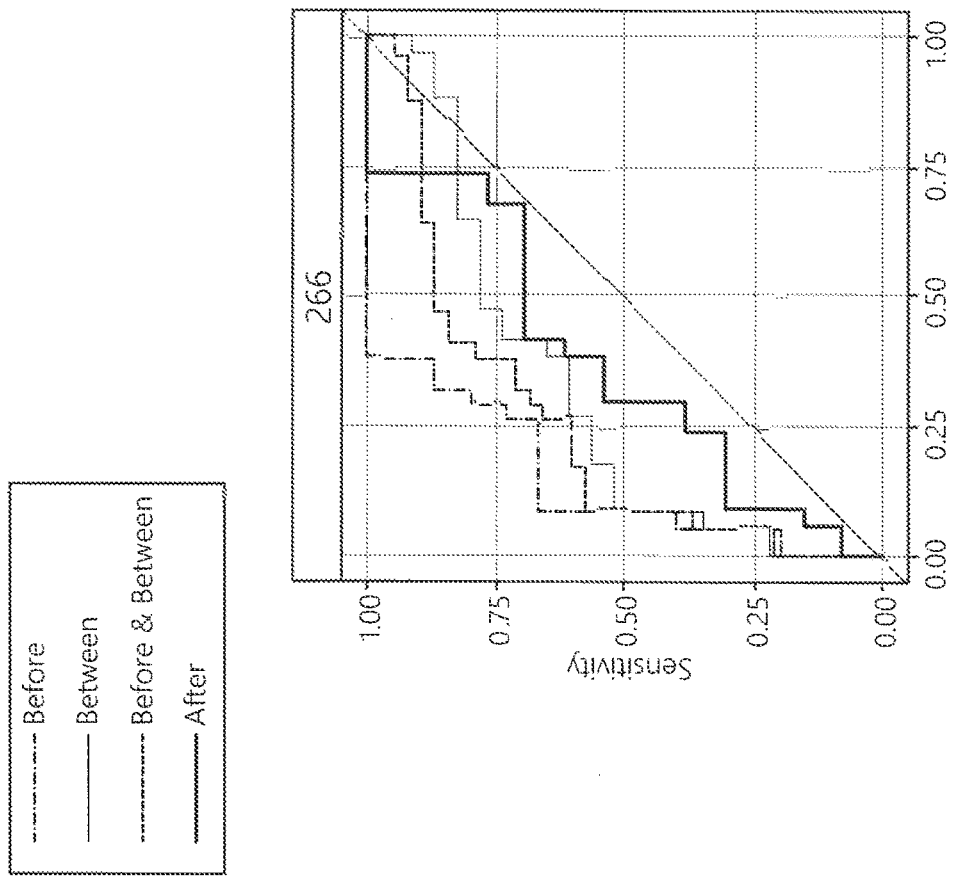
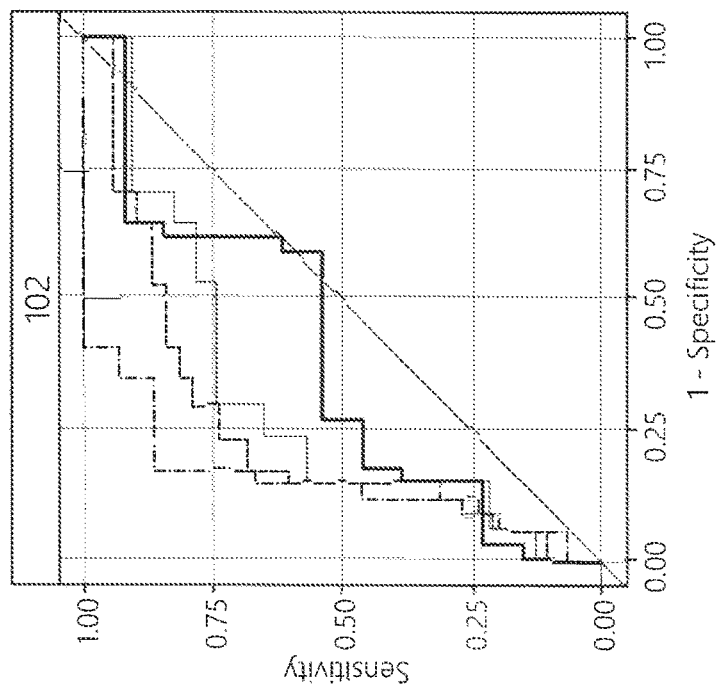
FIG. 3F
FIG. 3E

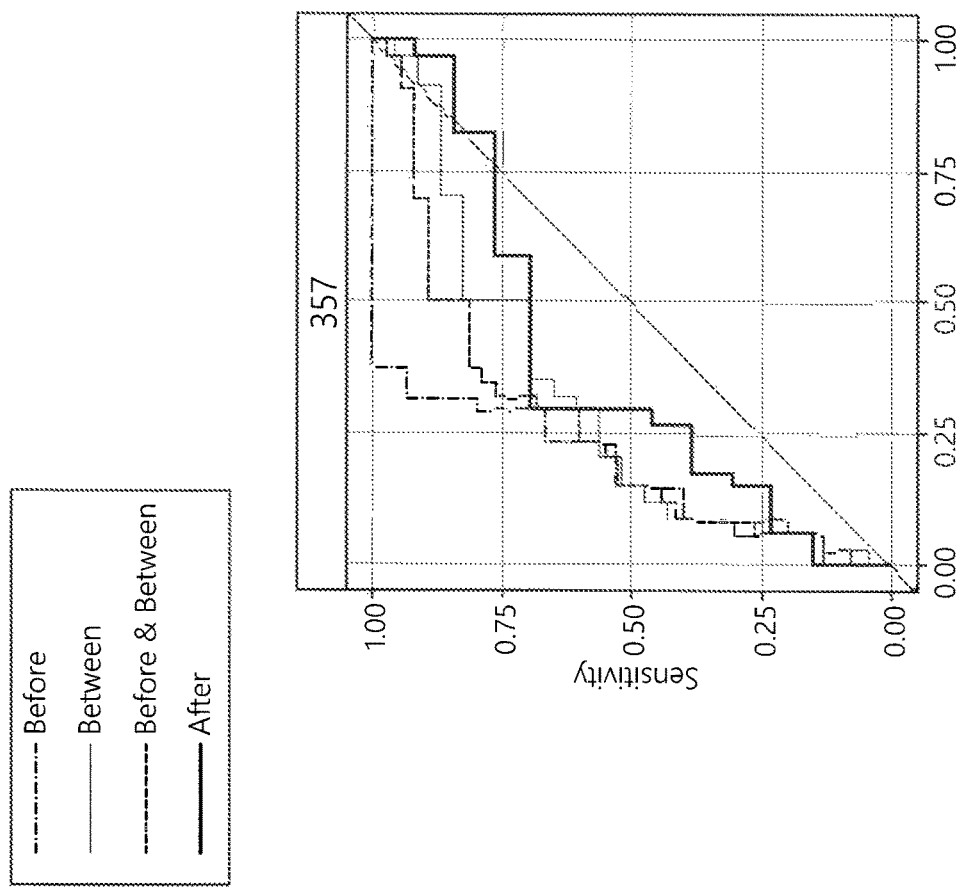
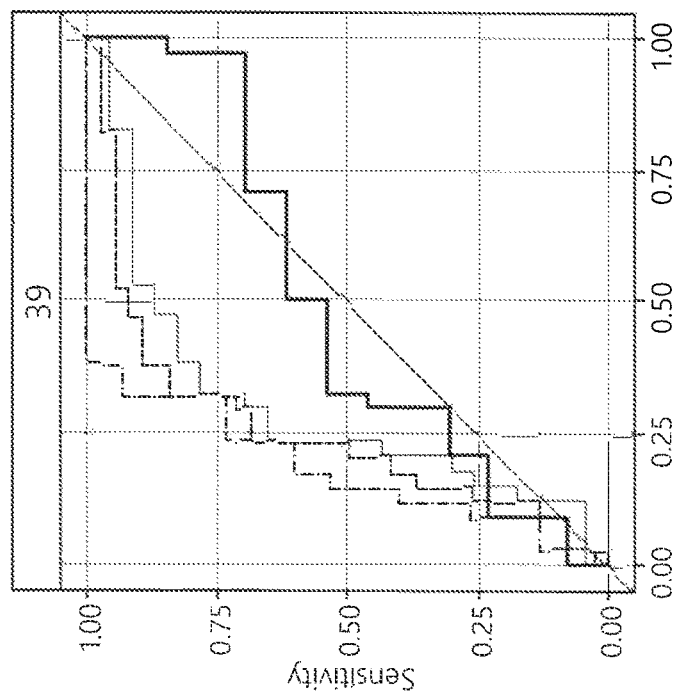
FIG. 3I
FIG. 3J

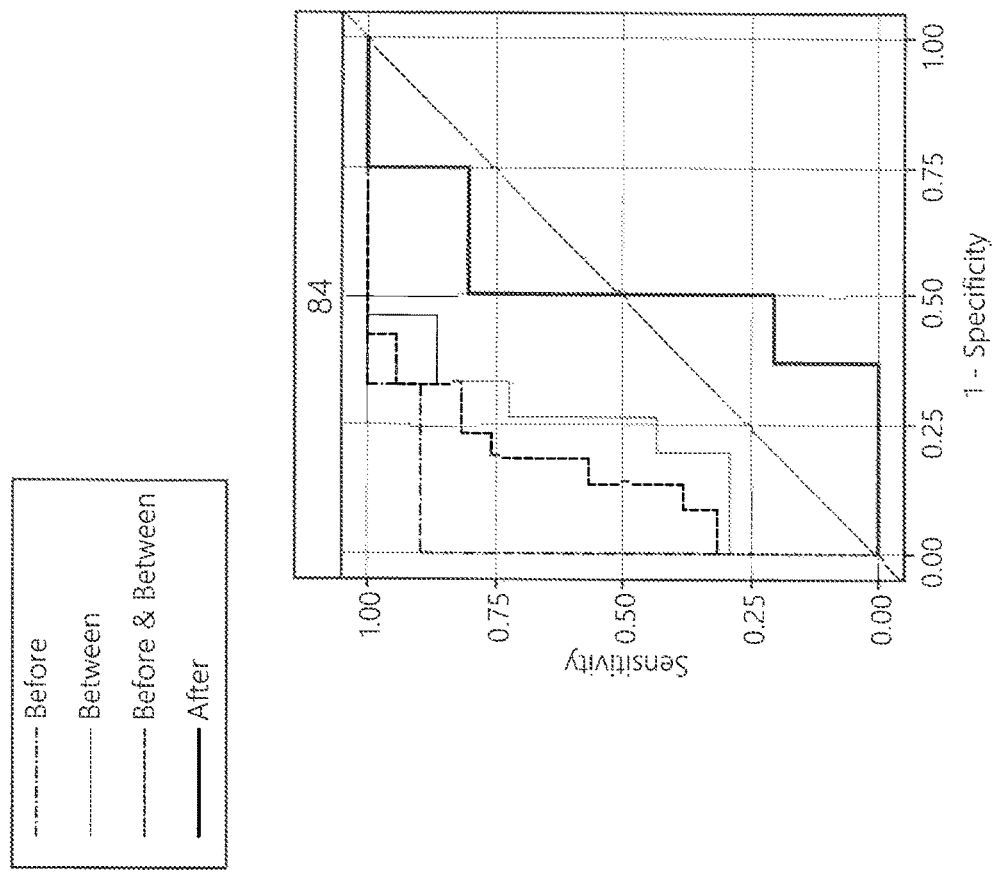
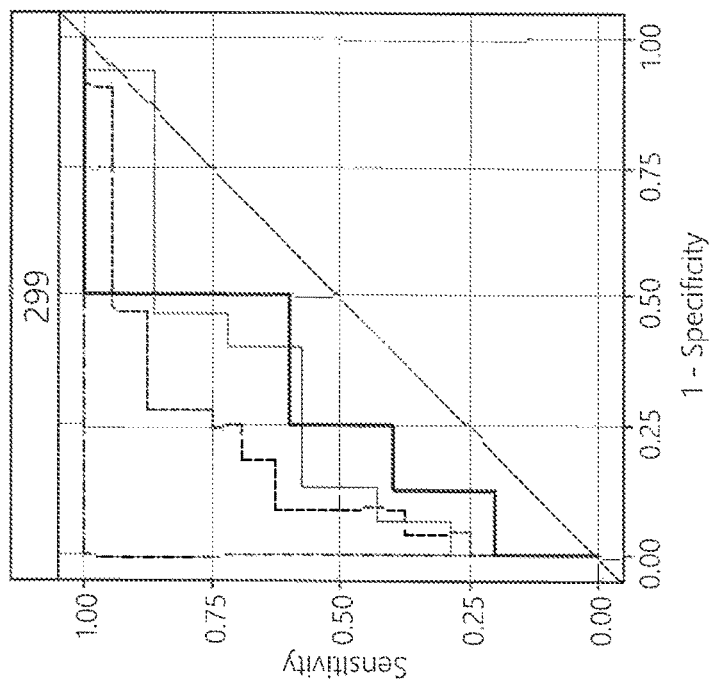
FIG. 7F
FIG. 7E

METHOD AND DEVICE FOR DIAGNOSING ORGAN INJURY

RELATED CASES

This application is a national stage application under 35 U.S.C. § 371 of International Application No. PCT/US2015/060311, filed on Nov. 12, 2015, which published in English as WO 2016/077537 A1 on May 19, 2016, and which claims the benefit of U.S. Provisional Application Ser. No. 62/078,810, filed on Nov. 12, 2014, the entire disclosure of which is incorporated by reference herein.

BACKGROUND

Field

Several embodiments of the present disclosure relate to devices and methods structured to isolate biomarkers from body fluids and methods of using the expression profiles of such biomarkers for diagnosis and treatment of diseases. Several embodiments relate to characterizing mRNA profiles of exosomes and microvesicles from urine samples to define underlying mechanisms of acute kidney injury (AKI).

Description of the Related Art

AKI is well recognized as a major complication in several diseases and settings affecting millions of patients worldwide. With the development of the diagnostic systems Risk, Injury, Failure, Loss of Function, End-stage disease (RIFLE), Acute Kidney Injury Network (AKIN), and Kidney Disease: Improving Global Outcomes (KDIGO), several reports have described the epidemiology of AKI in different settings. These have ranged from descriptions of administrative data sets, retrospective analysis of single and multicenter cohorts and prospective cohort studies. The staging system has been demonstrated to be a good predictor of outcomes with an increasing risk of mortality and resource utilization with higher stages regardless of the setting. Risk factors have included increasing age, presence of heart failure, liver failure and chronic kidney disease (CKD) and anemia and exposures to nephrotoxic agents including antibiotics, NSAIDS, and contrast agents. Infections, sepsis, shock, need for mechanical ventilation, and cardiac surgery are well recognized as high risk settings for development of AKI. A major concern with AKI is its association with adverse outcomes including the development of CKD. Several studies have demonstrated that non-recovery from AKI is associated with worse outcomes including higher mortality, reduced functional status and increased resource utilization. Recent evidences suggest that the underlying severity of injury and duration of AKI are important factors determining outcomes from AKI. For instance, Ishani et al categorized 29,388 post cardiac surgery patients from the Veterans Affairs Hospitals, patients based on serum creatinine increase from baseline. They showed a progressive increase in the hazard ratios for incident CKD, progression in CKD stage, and long-term mortality across the SCr categories, demonstrating that increasing the delta in serum creatinine there is an incremental risk for CKD development.

In many cases, physicians interpret a patient's symptoms, medical history and the results of a physical exam to derive an initial diagnosis. Medical tests are an integral part of confirming or modifying an initial diagnosis. Currently, some diagnostic medical tests are performed on blood extracted from a patient to determine disease from a biochemical pattern that is not present in healthy patients or is altered from a previously obtained patient sample. These tests commonly utilize plasma or serum and measure, for example electrolytes, urea, creatinine, and glucose. Other tests measure plasma proteins such as albumins, immunoglobulins, fibrinogens, and regulatory proteins. Still other tests measure other biological compounds, such as, for example, thiamin, riboflavin, niacin, vitamin B6, folic acid, vitamin D, biotin, iron, and clotting factors factor V and factor X.

Similarly, in the context of evaluating kidney function, measurement of the plasma concentrations of waste substances that should be removed by a functional kidney (such as creatinine and urea) or concentrations of electrolytes are often made to determine renal function. However, blood urea and creatinine levels often will not be raised above the normal range until a substantial amount (e.g., 40% or greater) of total kidney function is lost. Evaluation of glomerular filtration rate (GFR) or clearance of pharmacological marker compounds can also be used to evaluate kidney function. Analysis of 24 hour urine samples can also be used to evaluate kidney function. Another prognostic marker for kidney function is proteinuria, an elevated level of protein in the urine. Increasing amounts of proteins (such as albumin) in the urine indicate progressively increasing amounts of kidney damage, and associated loss of function.

SUMMARY

Generally, diagnostic tests are typically antibody based tests, commonly an ELISA, which may have limitations with respect to sensitivity. The combination of questionable assay accuracy at low assay target concentration ranges with the presumably low levels of creatinine (or other assay target) in the early stages of disease make it possible that diagnosis in early disease stages is not made. Additionally, certain diagnostic tests employ chemical reactions (e.g., colorimetric changes) to identify markers from blood or other fluid samples. Such tests may also be affected by similar limitations as are described above. Thus, there exists a need for a sensitive, accurate and reproducible diagnostic test for evaluating kidney function that enable early detection and/or diagnosis of compromised kidney function.

Moreover, there is a major imperative to focus efforts on enhancing renal recovery as early as possible to ensure a complete return of renal function. However, there are several gaps in existing knowledge of the pathophysiology and clinical course following AKI that contribute to non-recovery. In most cases renal recovery has been defined as a return of GFR without consideration of the tubular, hormonal and metabolic functions of the kidney. The cellular mechanisms responsible for the epidemiological association between AKI and CKD are complex. Pre-clinical studies have identified and characterized several pathways that are triggered following an injury to initiate repair and regeneration of the damaged tubules. However, based on the nature and severity of injury and underlying co-morbidities maladaptive repair and scarring may result. Despite the significant advances in experimental models, there is very limited knowledge in humans on the time sequence of recovery of different kidney segments, the cellular mechanisms involved and the factors that determine these events.

Recent advances in specific biomarkers reflecting functional change and structural damage now provide a unique set of tools to characterize events post AKI. Damage markers appear in urine and blood prior to elevation in serum creatinine (e.g. NGAL, Kim-1), represent site specificity of injury (e.g. Kim-1 for proximal tubule, Clusterin for collecting duct) and identify specific pathways involved (e.g. TIMP2 and IGFBP1 reflect cell cycle arrest). Several markers have been shown in small studies to correlate with prognosis following AKI however currently no specific markers have been identify patients at high risk for non-recovery.

Urinary EMV are a promising biomarker source for renal diseases because EMV are released throughout the nephrons by encapsulating the functional cytoplasmic molecules of the cell of origin. As discussed in more detail herein, several embodiments relate to a urinary EMV mRNA assay utilizing a proprietary filter material to capture EMV from urinary supernatant followed by mRNA isolation and quantification. Using this novel assay platform, biomarkers for AKI development as well as those to predict spontaneous recovery from AKI were screened and discovered.

EMV can be isolated from various biological fluids such as urine, blood, and saliva. EMV can protect the RNA enclosed therein from degradation by nucleases, allowing EMV to be used as potential non-invasive sources of biomarkers. In several embodiments, the detected biomarker can be used to develop an appropriate treatment regimen. In some embodiments, however, the treatment may be taking no further action (e.g., not instituting a treatment). In some embodiments, expression of a biomarker is detected by a method comprising liberating RNA from the isolated membrane particles, cells, exosomes, exosome-like vesicles, and/or microvesicles, contacting the liberated RNA with a reverse transcriptase to generate complementary DNA (cDNA), and contacting the cDNA with sense and antisense primers that are specific for the biomarker of the disease or condition to be treated and a DNA polymerase in order to generate amplified DNA. In several embodiments the methods are computerized (e.g., one or more of the RNA isolation, cDNA generation, or amplification are controlled, in whole or in part, by a computer). In several embodiments, the detection of the biomarker is real time. Additionally, in several embodiments, the method includes informing a medical professional of the test results, wherein the informing is performed by computer or other form of network communication. In several such embodiments, the computers (or tablets, smartphones, etc.) involved in transmitting or receiving of the expression information comprise a dynamic graphical user interface that provides the physician with therapeutic options for treating the subject, when appropriate and allows the physician to filter or otherwise refine the information provided based on therapeutic preferences derived from characteristics specific to the subject.

Based on these needs, there is provided herein a method for enabling a medical professional to recommend or not recommend a therapy to a subject based on the biomarker profile obtained from the subject's body-fluid sample. In several embodiments, urinary exosomes and microvesicles are used as a biomarker source to define the underlying pathways contributing to organ damage. In several embodiments, exosome and microvesicle mRNA in urines of hospitalized patients in different pathophysiological settings is analyzed to discover new diagnostic biomarkers. In at least one embodiment, urinary exosome and microvesicle mRNA from urines of patients in different AKI settings is characterized to identify mRNA expression profiles that correlate to AKI. Methods and devices for capture of exosomes and microvesicles are disclosed in International Application PCT/US2014/058404, filed on Sep. 30, 2014, the contents of which are herein incorporated by reference.

In several embodiments, there are also provided methods for characterizing kidney function of the patient, the method comprising, obtaining a first sample of urine from a patient, wherein the sample comprises vesicles that are associated with RNA, capturing the vesicles from the first urine sample, lysing the vesicles to release the vesicle-associated RNA, wherein the vesicle-associated RNA comprises an RNA associated with kidney function, quantifying the RNA associated with kidney function, comparing the amount of the RNA associated with kidney function from the patient to the quantity of a corresponding RNA from individuals having normal kidney function, wherein a difference in the quantity of the RNA associated with kidney function between the patient and the individuals indicates a change in kidney function of the patient, and wherein a lack of a difference in the quantity of the RNA associated with kidney function between the patient and the individuals indicates that the kidney function of the patient is normal; and 1) indicating to the medical professional when there is a change in the kidney function of the patient, or 2) indicating to the medical professional when the kidney function of patient is normal, thereby enabling a medical professional to recommend a therapy or forego recommending a therapy to the patient based on the kidney function of the patient.

In some embodiments, the EMV are isolated from the biological fluid sample using one or more types of physical force. In some embodiments, a syringe or syringe-like device is used to isolate the material (e.g., via suction or, alternatively, via positive pressure). In other embodiments, centrifugation, shaking, air pressure, or liquid pressure are used. Combinations may also be used, in several embodiments. In some embodiments, EMV are isolated from the biological fluid sample by filtering the sample. In some embodiments, filtering the collected sample will trap one or more of membrane particles, exosomes, exosome-like vesicles, and microvesicles on a filter. In some embodiments, the filter comprises material to capture components that are about 1.6 microns or greater in diameter. In several embodiments, a plurality of filters is used to capture vesicles within a particularly preferred range of sizes (e.g., diameters). For example, in several embodiments, filters are used to capture vesicles having a diameter of from about 0.2 microns to about 1.6 microns in diameter, including about 0.2 microns to about 0.4 microns, about 0.4 microns to about 0.6 microns, about 0.6 microns to about 0.8 microns, about 0.8 microns to about 1.0 microns, about 1.0 microns to about 1.2 microns, about 1.2 to about 1.4 microns, about 1.4 microns to about 1.6 microns (and any size in between those listed). In other embodiments, the vesicle-capture material captures exosomes ranging in size from about 0.5 microns to about 1.0 microns.

In some embodiments, the filter (or filters) comprises glass-like material, non-glass-like material, or a combination thereof. In some embodiments, wherein the vesicle-capture material comprises glass-like materials, the vesicle-capture material has a structure that is disordered or "amorphous" at the atomic scale, like plastic or glass. Glass-like materials include, but are not limited to glass beads or fibers, silica beads (or other configuration), nitrocellulose, nylon, polyvinylidene fluoride (PVDF) or other similar polymers, metal or nano-metal fibers, polystyrene, ethylene vinyl acetate or other co-polymers, natural fibers (e.g., silk), alginate fiber, or combinations thereof. In certain embodiments, the vesicle-capture material optionally comprises a plurality of layers of vesicle-capture material. In other embodiments, the vesicle-capture material further comprises nitrocellulose.

In some embodiments, a filter device is used to isolate biological components of interest. In some embodiments, the device comprises: a first body having an inlet, an outlet, and an interior volume between the inlet and the outlet; a second body having an inlet, an outlet, an interior volume between the inlet and the outlet, a filter material positioned within the interior volume of the second body and in fluid communication with the first body; and a receiving vessel having an inlet, a closed end opposite the inlet and interior cavity. In some embodiments, the first body and the second body are reversibly connected by an interaction of the inlet of the second body with the outlet of the first body. In some embodiments, the interior cavity of the receiving vessel is dimensioned to reversibly enclose both the first and the second body and to receive the collected sample after it is passed from the interior volume of the first body, through the filter material, through the interior cavity of the second body and out of the outlet of the second body. In some embodiments, the isolating step comprises placing at least a portion of the collected sample in such a device, and applying a force to the device to cause the collected sample to pass through the device to the receiving vessel and capture the biological component of interest. In some embodiments, applying the force comprises centrifugation of the device. In other embodiments, applying the force comprises application of positive pressure to the device. In other embodiments, applying the force comprises application of vacuum pressure to the device. Non-limiting examples of such filter devices are disclosed in PCT Publication WO 2014/182330 and PCT Publication WO 2015/050891, hereby incorporated by reference herein.

In some embodiments, the collected sample is passed through multiple filters to isolate the biological component of interest. In other embodiments, isolating biological components comprises diluting the collected sample. In other embodiments, centrifugation may be used to isolate the biological components of interest. In some embodiments, multiple isolation techniques may be employed (e.g., combinations of filtration selection and/or density centrifugation). In some embodiments, the collected sample is separated into one or more samples after the isolating step.

In some embodiments, RNA is liberated from the biological component of interest for measurement. In some embodiments, liberating the RNA from the biological component of interest comprises lysing the membrane particles, exosomes, exosome-like vesicles, and/or microvesicles with a lysis buffer. In other embodiments, centrifugation may be employed. In some embodiments, the liberating is performed while the membrane particles, exosomes, exosome-like vesicles, microvesicles and/or other components of interest are immobilized on a filter. In some embodiments, the membrane particles, exosomes, exosome-like vesicles, microvesicles and/or other components of interest are isolated or otherwise separated from other components of the collected sample (and/or from one another—e.g., vesicles separated from exosomes).

In several embodiments, the liberated RNA comprises one or more marker mRNAs that encodes a marker selected from the group consisting of ALB, AQP1, AQP2, B2M, CALB1, CALM1, CFLAR, CLU, CST3, CXCL1, CXCL3, EGF, GSTA1, HIF1A, IL1B, IL18, LGALS3, LGALS3BP, MYD88, NLRP3, PKM, PPIA, RAC2, RIPK1, S100A9, SLC12A1, TNFRSF1A, and VCAM1. In several aspects, the biological fluid is selected from the group consisting of blood, urine, saliva, and intestinal fluid.

In some embodiments, the RNA liberated from the biological components of interest comprises poly(A)+ RNA.

According to various embodiments, various methods to quantify RNA are used, including Northern blot analysis, RNAse protection assay, PCR, RT-PCR, real-time RT-PCR, other quantitative PCR techniques, RNA sequencing, nucleic acid sequence-based amplification, branched-DNA amplification, mass spectrometry, CHIP-sequencing, DNA or RNA microarray analysis and/or other hybridization microarrays. In some of these embodiments or alternative embodiments, after amplified DNA is generated, it is exposed to a probe complementary to a portion of a biomarker of interest.

In some embodiments, a computerized method is used to complete one or more of the steps. In some embodiments, the computerized method comprises exposing a reaction mixture comprising isolated RNA and/or prepared cDNA, a polymerase and gene-specific primers to a thermal cycle. In some embodiments, the thermal cycle is generated by a computer configured to control the temperature time, and cycle number to which the reaction mixture is exposed. In other embodiments, the computer controls only the time or only the temperature for the reaction mixture and an individual controls on or more additional variables. In some embodiments, a computer is used that is configured to receive data from the detecting step and to implement a program that detects the number of thermal cycles required for the biomarker to reach a pre-defined amplification threshold in order to identify whether a subject is suffering from AKI. In still additional embodiments, the entire testing and detection process is automated.

For example, in some embodiments, RNA is isolated by a fully automated method, e.g., methods controlled by a computer processor and associated automated machinery. In one embodiment a biological sample, such as urine, is collected and loaded into a receiving vessel that is placed into a sample processing unit. A user enters information into a data input receiver, such information related to sample identity, the sample quantity, and/or specific patient characteristics. In several embodiments, the user employs a graphical user interface to enter the data. In other embodiments, the data input is automated (e.g., input by bar code, QR code, or other graphical identifier). The user can then implement an RNA isolation protocol, for which the computer is configured to access an algorithm and perform associated functions to process the sample in order to isolate biological components, such as vesicles, and subsequently processed the vesicles to liberate RNA. In further embodiments, the computer implemented program can quantify the amount of RNA isolated and/or evaluate and purity. In such embodiments, should the quantity and/or purity surpass a minimum threshold, the RNA can be further processed, in an automated fashion, to generate cDNA. cDNA can then be generated, such as for example, binding of a poly-A RNA tail to an oligo dT molecule and subsequent extension using an RNA polymerase. In other embodiments, if the quantity and/or purity fail to surpass a minimum threshold, the computer implemented program can prompt a user to provide additional biological sample(s).

Depending on the embodiment, the cDNA can be divided into individual subsamples, some being stored for later analysis and some being analyzed immediately. Analysis, in some embodiments comprises mixing a known quantity of the cDNA with a salt-based buffer, a DNA polymerase, and at least one gene specific primer to generate a reaction mixture. The cDNA can then be amplified using a predetermined thermal cycle program that the computer system is configured to implement. This thermal cycle, could optionally be controlled manually as well. After amplification (e.g., real-time PCR), the computer system can assess the number of cycles required for a gene of interest (e.g. a marker of AKI) to surpass a particular threshold of expression. A data analysis processor can then use this assessment to calculate the amount of the gene of interest present in the original sample, and by comparison either to a different patient sample, a known control, or a combination thereof, expression level of the gene of interest can be calculated. A data output processor can provide this information, either electronically in another acceptable format, to a test facility and/or directly to a medical care provider. Based on this determination, the medical care provider can then determine if and how to treat a particular patient based on determining the presence of an AKI. In several embodiments, the expression data is generated in real time, and optionally conveyed to the medical care provider (or other recipient) in real time.

In several embodiments, a fully or partially automated method enables faster sample processing and analysis than manual testing methods. In certain embodiments, machines or testing devices may be portable and/or mobile such that a physician or laboratory technician may complete testing outside of a normal hospital or laboratory setting. In some embodiments, a portable assay device may be compatible with a portable device comprising a computer such as a cell phone or lap top that can be used to input the assay parameters to the assay device and/or receive the raw results of a completed test from the assay device for further processing. In some embodiments, a patient or other user may be able to use an assay device via a computer interface without the assistance of a laboratory technician or doctor. In these cases, the patient would have the option of performing the test "at-home." In certain of these embodiments, a computer with specialized software or programming may guide a patient to properly place a sample in the assay device and input data and information relating to the sample in the computer before ordering the tests to run. After all the tests have been completed, the computer software may automatically calculate the test results based on the raw data received from the assay device. The computer may calculate additional data by processing the results and, in some embodiments, by comparing the results to control information from a stored library of data or other sources via the internet or other means that supply the computer with additional information. The computer may then display an output to the patient (and/or the medical care provider, and/or a test facility) based on those results.

In some embodiments, a medical professional may be in need of genetic testing in order to diagnose, monitor and/or treat a patient. Thus, in several embodiments, a medical professional may order a test and use the results in making a diagnosis or treatment plan for a patient. For example, in some embodiments a medical professional may collect a sample from a patient or have the patient otherwise provide a sample (or samples) for testing. The medical professional may then send the sample to a laboratory or other third party capable of processing and testing the sample. Alternatively, the medical professional may perform some or all of the processing and testing of the sample himself/herself (e.g., in house). Testing may provide quantitative and/or qualitative information about the sample, including data related to the presence of an AKI. Once this information is collected, in some embodiments the information may be compared to control information (e.g., to a baseline or normal population) to determine whether the test results demonstrate a difference between the patient's sample and the control. After the information is compared and analyzed, it is returned to the medical professional for additional analysis. Alternatively, the raw data collected from the tests may be returned to the medical professional so that the medical professional or other hospital staff can perform any applicable comparisons and analyses. Based on the results of the tests and the medical professional's analysis, the medical professional may decide how to treat or diagnose the patient (or optionally refrain from treating).

In some embodiments, expression of a biomarker is compared to expression of the biomarker in a control sample. In some embodiments, the control sample is based on the expression of the biomarker in a healthy individual, or an individual who is not suffering from an AKI. In other embodiments, the control sample is based on an average or control RNA expression profile generated based on the average biomarker expression of multiple healthy individuals. In other embodiments, the control sample is based on the expression of the biomarker in an individual who is suffering from an AKI. In other embodiments, the control sample is generated by a computer that has received data for subjects whose biomarker expression levels have been analyzed. In some embodiments, multiple samples are taken from the same individual at different times over the course of days, weeks, months, or years. In these embodiments, the earlier data collected may be used to generate a control sample to compare to the later data. In addition, these multiple samples can be used to track whether (and how) mRNA expression changes in a patient over time.

In some embodiments, an mRNA expression profile is generated for one or more mRNA associated with an AKI or any other biomarkers. In some embodiments, the mRNA expression profile may be generated to include a comparison of the expression of a biomarker in an individual to the expression of the biomarker in a control sample, where the control sample is generated by any of the methods described above or through alternative means that similarly provide a data reference point. In some embodiments, an mRNA expression profile may be based on mRNA data collected from the individual patient alone, where expression data was collected on either one or multiple occasions.

In some embodiments, greater expression of a biomarker indicates a subject is suffering from an AKI. In other embodiments, reduced expression of a biomarker indicates a subject is suffering from an AKI. Depending on the marker, and the embodiment, increases or decreases in expression may be statistically significant (e.g., p-values less than 0.05 by art-accepted statistical analysis methods). In some embodiments, expression is compared against a control value or expression profile to determine whether a subject is suffering from an AKI compared to the control. In some embodiments, expression indicating AKI or lack thereof is corroborated with a histological evaluation of a biopsy of a cell or tissue population of interest.

In some embodiments, the AKI is treated with oral, intravenously administered, systemically administered or locally administered medication. Medications are not limited to a compound that is generally considered of medicinal purpose (e.g., a prescribed or over the counter drug) but may also include any dietary or nutrition supplement(s). Therefore, for example, a vitamin, a mineral, an herb or other botanical, an amino acid, a dietary substance for use by a subject to supplement the diet by increasing the total dietary intake (e.g., enzymes or tissues from organs or glands), or a concentrate, metabolite, constituent or extract can also be applicable to the methods disclosed herein. In other embodiments, the AKI is treated with surgery or further inspection of the subject, such as with ultrasound. In some embodiments, the subject is treated using renal replacement therapy, dialysis, or combinations thereof. In some embodiments, the subject is treated by administering a diuretic agent (e.g., furosemide), an intravenous fluid, a steroid medication, a plasma exchange, a cyclophosphamide, or combinations thereof.

There is also provided herein a method for characterizing kidney function comprising obtaining at least two samples of urine from a patient, wherein the samples comprise vesicles that are associated with RNA, isolating the vesicles from the samples, lysing the vesicles to release the vesicle-associated RNA, wherein the vesicle-associated RNA comprises an RNA associated with kidney function and an RNA that does not change in response to kidney function, quantifying the RNA associated with kidney function and the RNA that does not change in response to kidney function; and determining a ratio between the amount of the RNA associated with kidney function from the patient and the quantity of an RNA that does not change in response to kidney function, wherein a difference in the ratio between the two or more urine samples indicates a change in kidney function of the patient.

In one embodiment, the RNA that does not change in response to kidney function is one of beta-actin or beta-2-microglobulin.

In several embodiments, the kidney function is altered due to disease, the disease selected from the group consisting of AKI, chronic kidney disease, acute renal failure, diabetic nephropathy, glomerulonephritis, glomerulosclerosis, focal segmental glomerulosclerosis, membranous nephropathy, minimal change disease, and kidney disease secondary to other diseases such as atherosclerosis, hypertension, cardiovascular diseases, obesity, hypercholesterolemia, diabetes, liver diseases, collagen diseases, autoimmune disease, and infection. In some embodiments, the kidney function is altered due to administration of a pharmacological agent to the patient.

In several embodiments, the kidney function is altered due to kidney damage. In some embodiments, the kidney damage comprises one or more of damage to the glomerulus, damage to the endothelium, damage to the proximal tubule, damage to the loop of Henle, damage to the collecting duct, and damage to the ureter. In several embodiments, the kidney function is altered due to changes in blood flow into or out of the kidney.

In several embodiments, isolating the vesicles from the sample comprises filtering the urine. In some embodiments, the filtration traps the vesicles on a filter. In several embodiments, the lysing is performed while the vesicles are trapped on the filter. In several embodiments, the methods further comprise centrifuging the sample to remove cellular debris and filtering the supernatant of the centrifuged urine. In one embodiment, the centrifugation is performed prior to isolating the vesicles. In several embodiments, the concentrating of the vesicles further comprises filtering the supernatant of the centrifuged urine.

In several embodiments, the vesicles are isolated by a method comprising loading at least a portion of the first sample of urine into a sample loading region of a vesicle capture device, passing the urine from the sample loading region through a vesicle-capture material in the vesicle capture device, the vesicle-capture material comprising glass-like materials to produce a supernatant, passing the supernatant to a sample receiving region of the vesicle capture device and discarding the supernatant, wherein the passings result in capture of the vesicles from the urine sample on or in the vesicle-capture material, thereby capturing the vesicles.

In some embodiments, the vesicle-capture material comprises a plurality of layers of the material. In several embodiments the plurality of layers of the vesicle-capture material comprises at least a first layer and a second layer of glassfiber. In several embodiments, the biological fluid is passed through the first layer of glassfiber so as to capture material from the biological sample that is about 1.6 microns or greater in diameter. In several embodiments, the biological fluid is passed through the second layer of glassfiber so as to capture vesicles having a minimum size from about 0.6 microns to about 0.8 microns in diameter, and having a maximum size of less than 1.6 microns.

In some embodiments, microvesicle mRNA is quantified by a method selected from the group consisting of reverse-transcription polymerase chain reaction (RT-PCR), real-time RT-PCR, northern blotting, fluorescence activated cell sorting, ELISA, and mass spectrometry. In one embodiment, the quantifying comprises amplifying the RNA using RT-PCR. In several embodiments, the RNA comprises poly(A)+ RNA.

In several embodiments, there are also provided methods for identifying new diagnostic biomarkers, the method comprising, selecting a sample population of patients displaying different known AKI settings, obtaining urine samples from patients with different known AKI settings, purifying exosomes and microvesicles from the urine samples, quantifying exosome and microvesicle mRNA expression of a panel of target genes, correlating mRNA expression levels of each target gene to the known AKI setting of the source patient, generating Receiver Operator Characteristic (ROC) curves for different combinations of target genes, using cross-validation to calculate Area Under the Curve (AUC) for the ROC curves, and ranking specificity and sensitivity of the target gene combinations in relation to diagnosis of the underlying AKI setting of the source patient.

In some embodiments, the above-mentioned correlation method is used to identify biomarkers that predict development of kidney dysfunction with high sensitivity and specificity. In some embodiments, combinations of biomarkers are identified to predict recovery of kidney function with high sensitivity and specificity. In at least one embodiment, combinations of biomarkers are identified to predict development of AKI with high sensitivity and specificity. In at least one embodiment, combinations of biomarkers are identified to predict recovery of kidney function from AKI with high sensitivity and specificity. In at least one embodiment, AKI is evaluated by analyzing urinary exosome and microvesicle mRNA expression of Calmodulin 1 (CALM1), Aquaporin 2 (AQP2), and Osteopontin (SPP1).

The methods summarized above and set forth in further detail below describe certain actions taken by a practitioner; however, it should be understood that they can also include the instruction of those actions by another party. Thus, actions such as "treating a subject for a disease or condition" include "instructing the administration of treatment of a subject for a disease or condition."

BRIEF DESCRIPTION OF THE DRAWINGS

FIGS. 1A-1D show urinary EMV mRNA expression profiles among AKI, no AKI, and healthy control populations.

FIGS. 2A-2F show ROC curve analysis of AKI development markers from urinary EMV.

FIGS. 3A-3J show ROC curve analysis of AKI development gene classifiers from urinary EMV.

FIG. 7A-7J show ROC curve analysis of AKI recovery gene classifiers from urinary EMV.

DETAILED DESCRIPTION

General

Figures 1A, 1B:
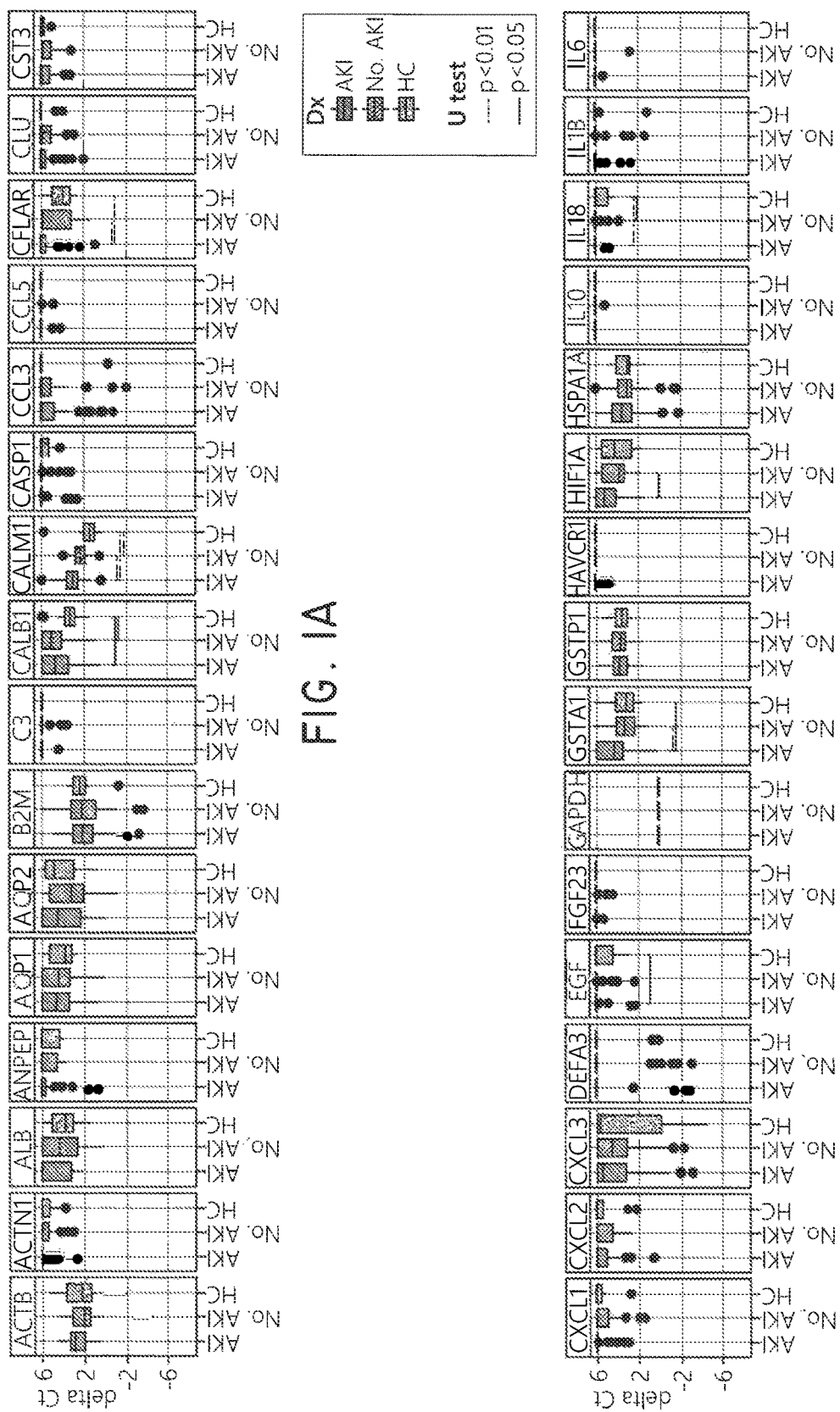
Figure 2D:
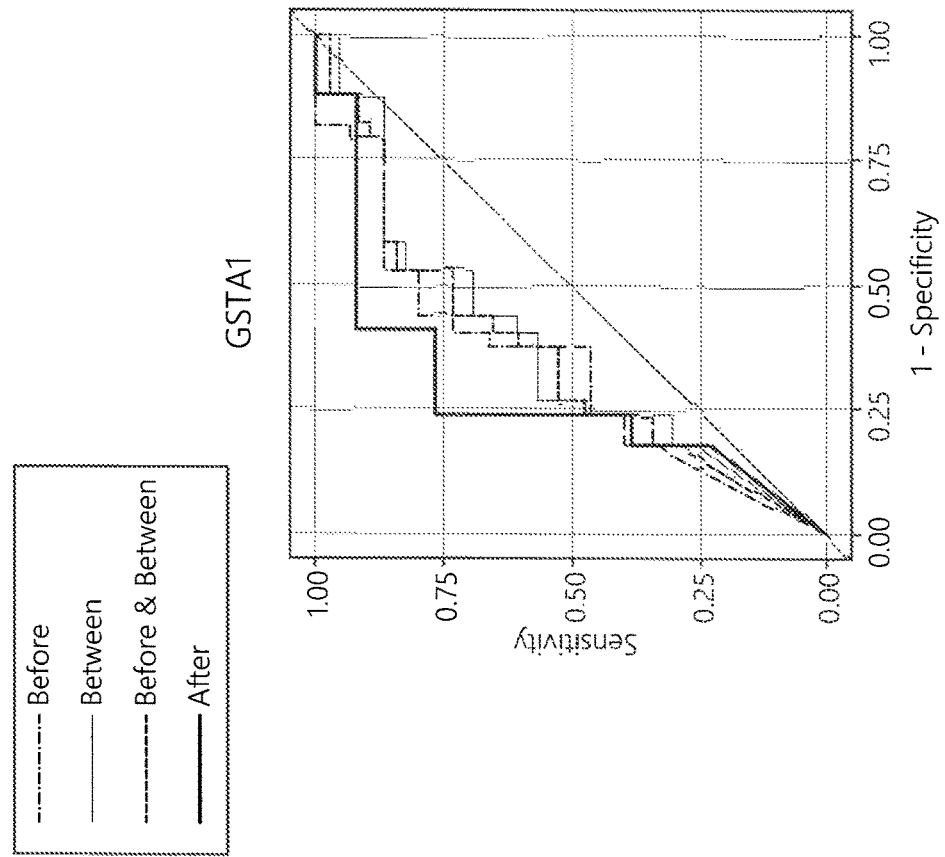
Figure 2C:
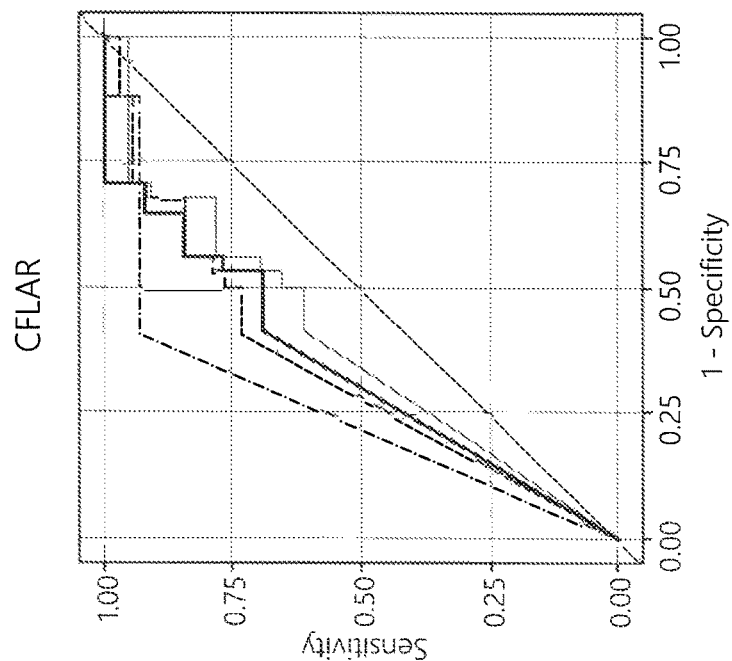
Figure 3D:
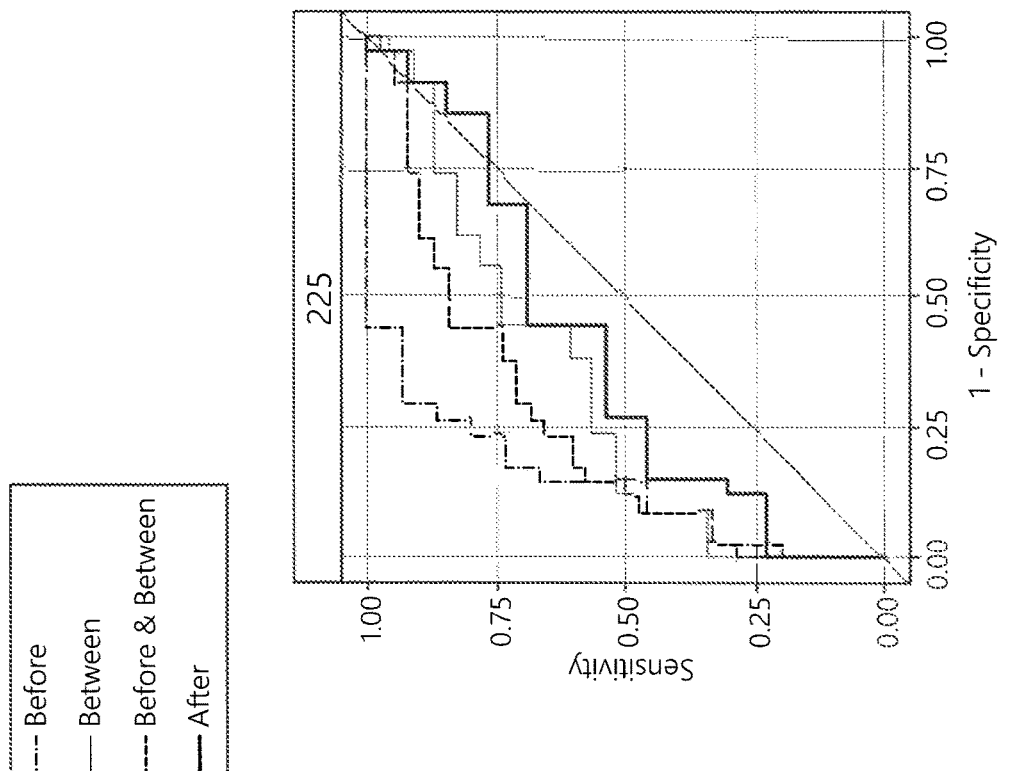
Figure 3C:
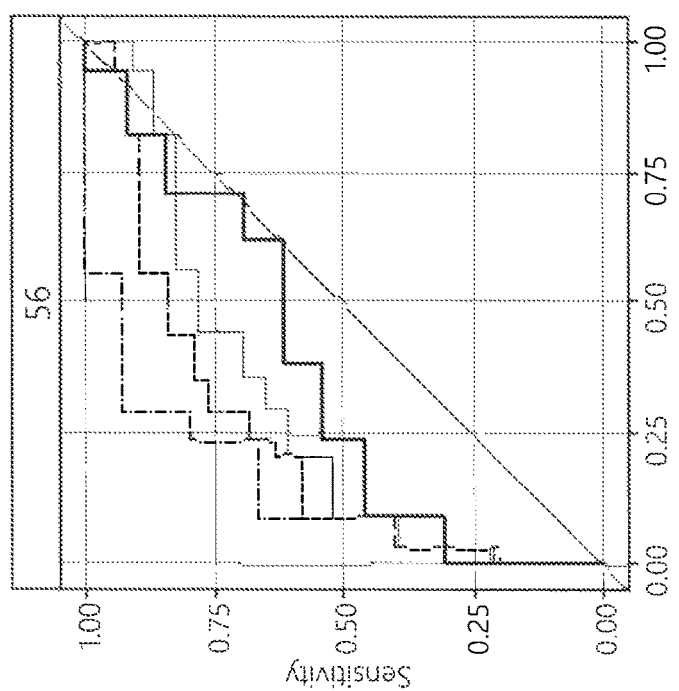
Figure 3H:
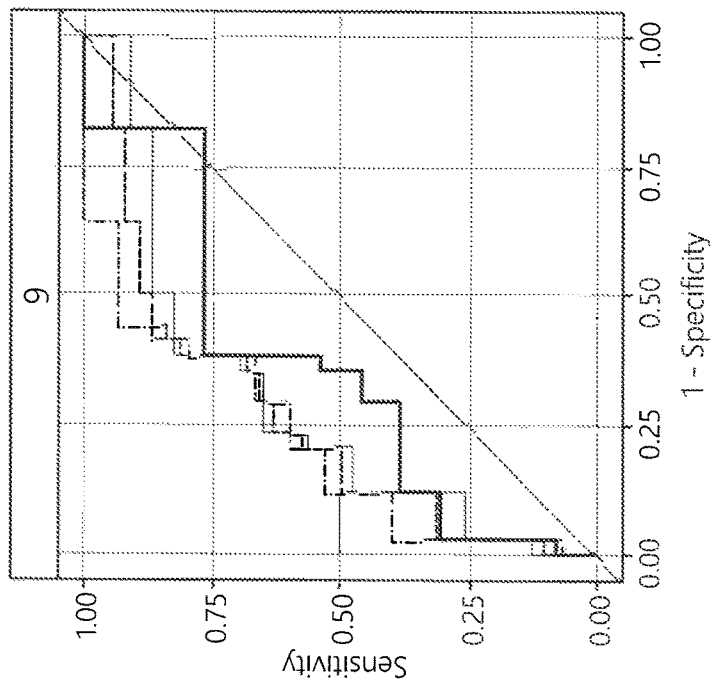
Figure 3G:
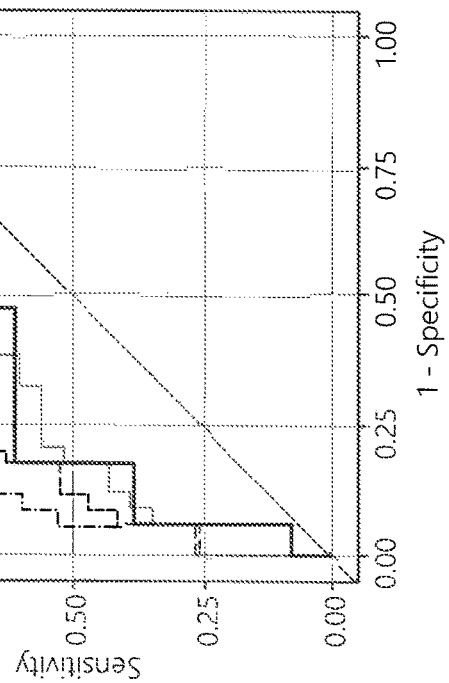
Figures 4A, 4B:
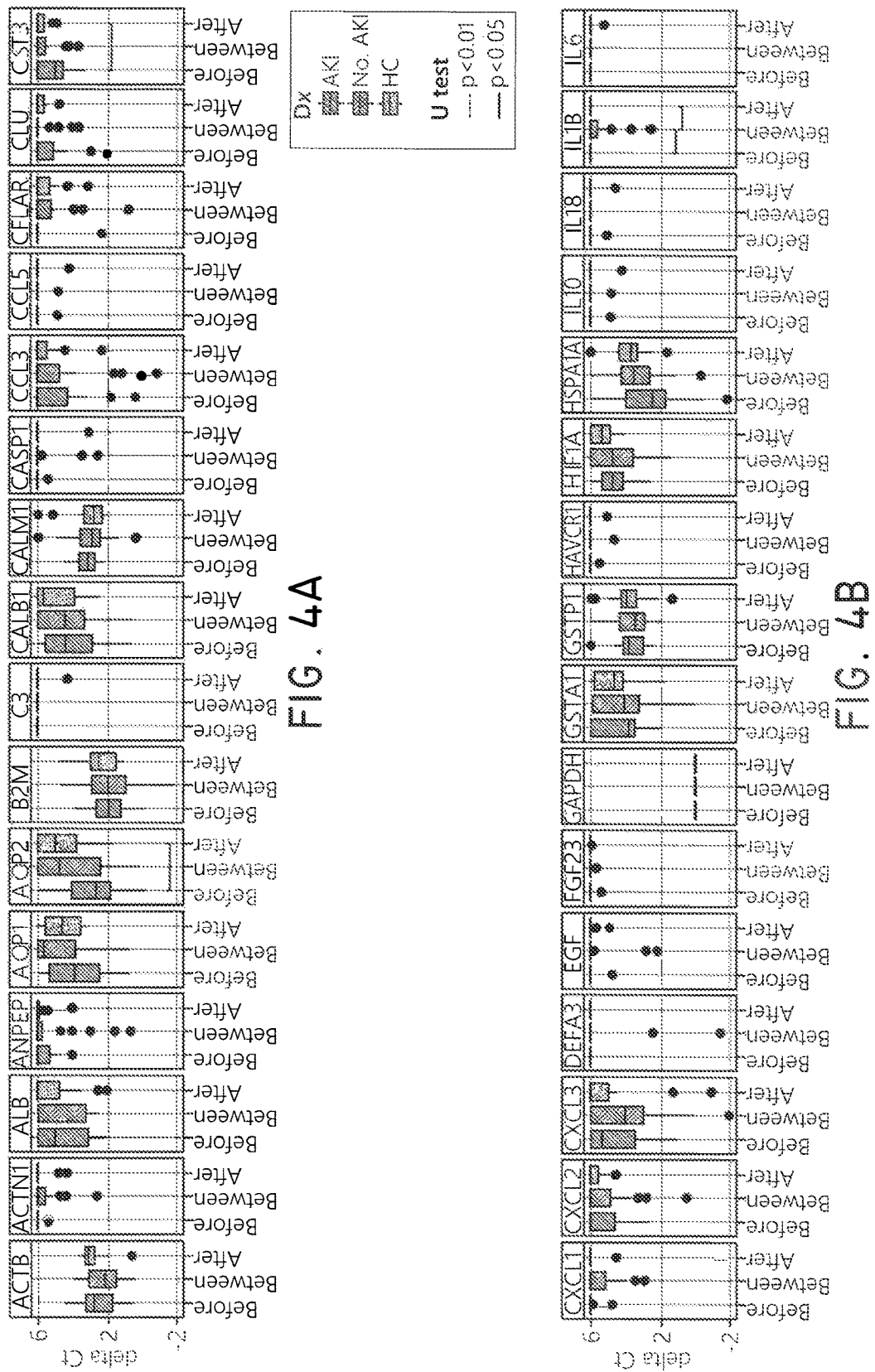
FIG. 4A-4D show urinary EMV mRNA expression profiles for the Before, Between, and After sub-groups of the AKI population.
Figures 4C, 4D:
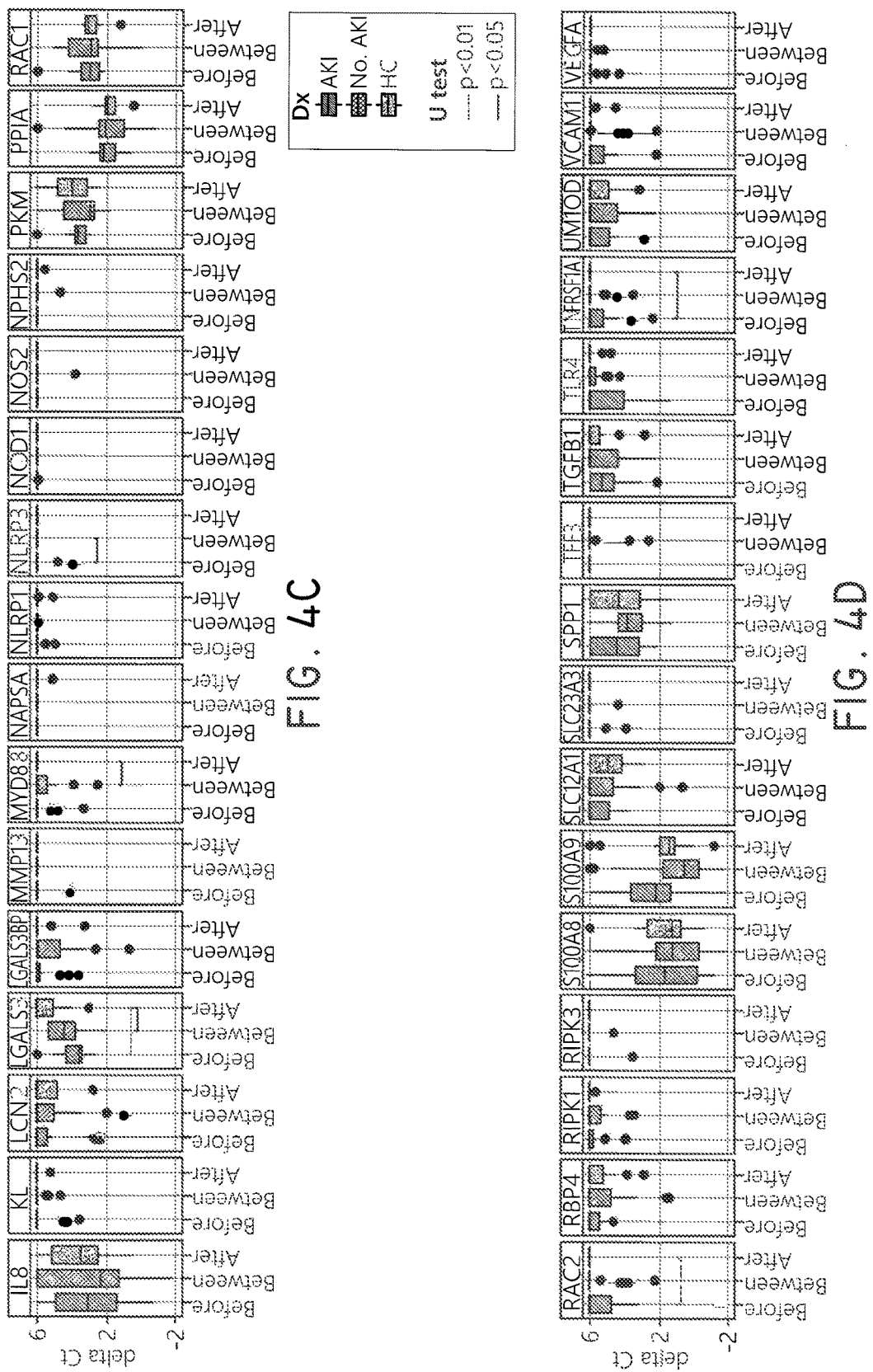
Figure 5A:
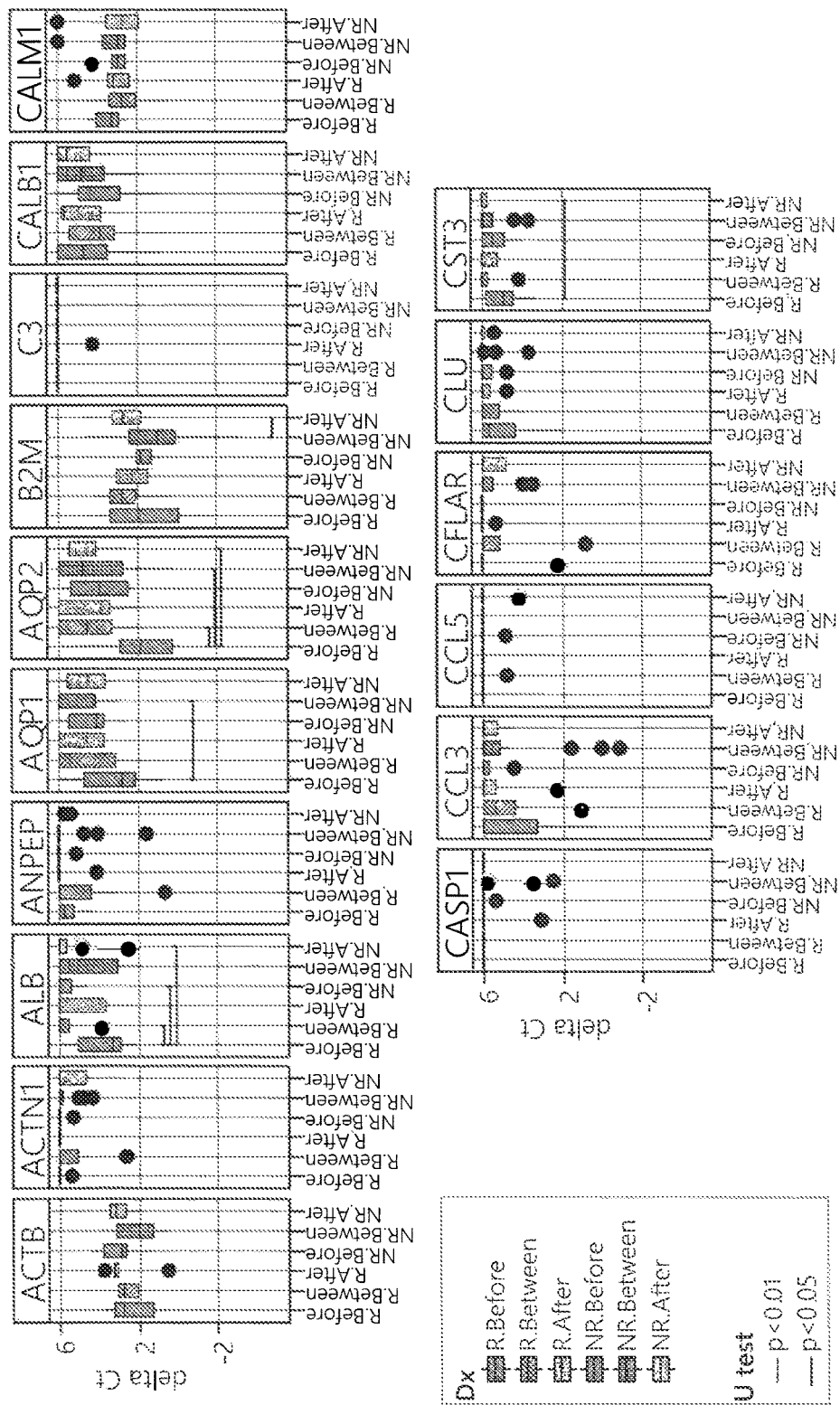
FIGS. 5A-5D show urinary EMV mRNA expression profiles for Recovery and non-Recovery sub-groups of the AKI population.
Figure 5B:
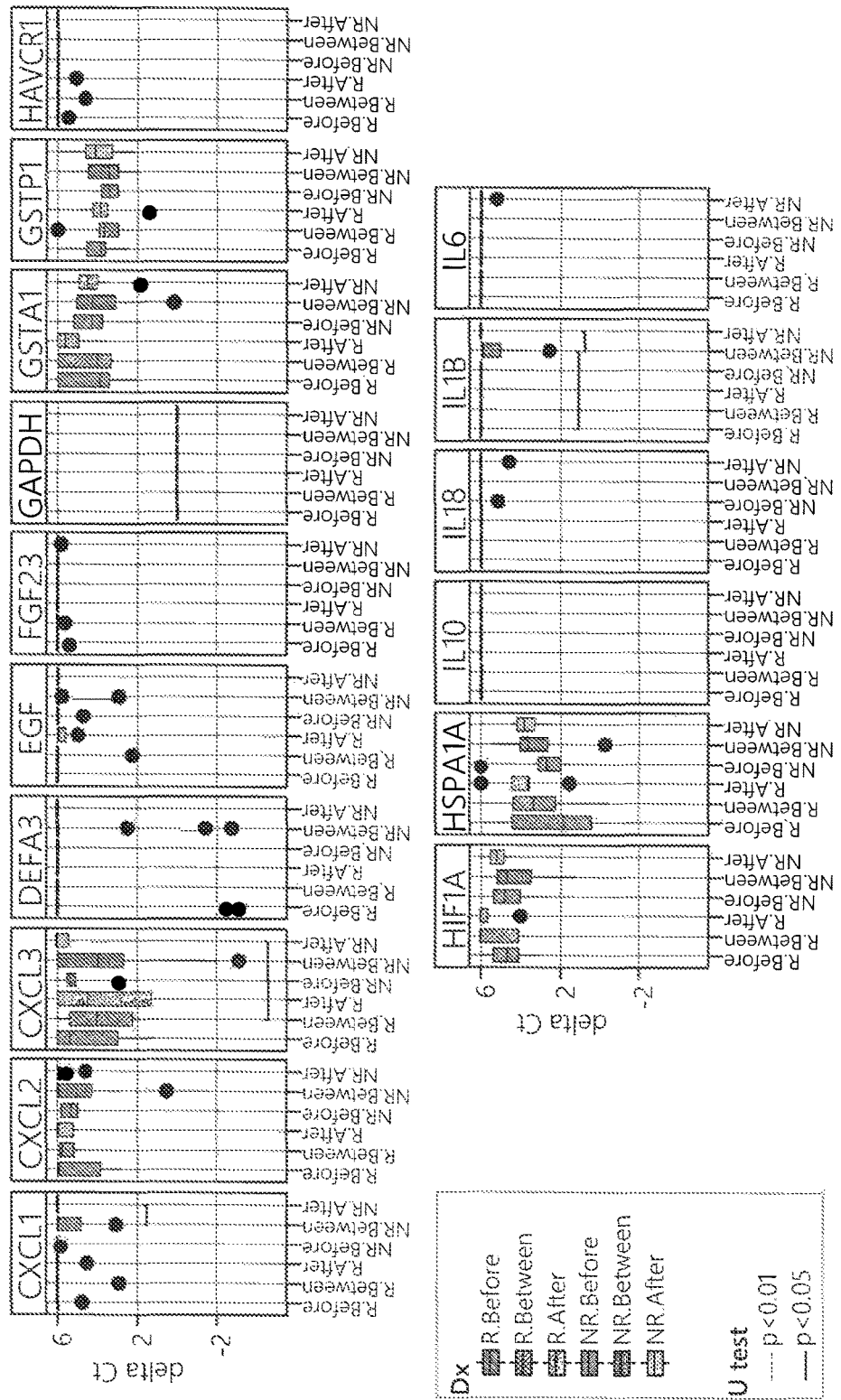
Figure 5C:
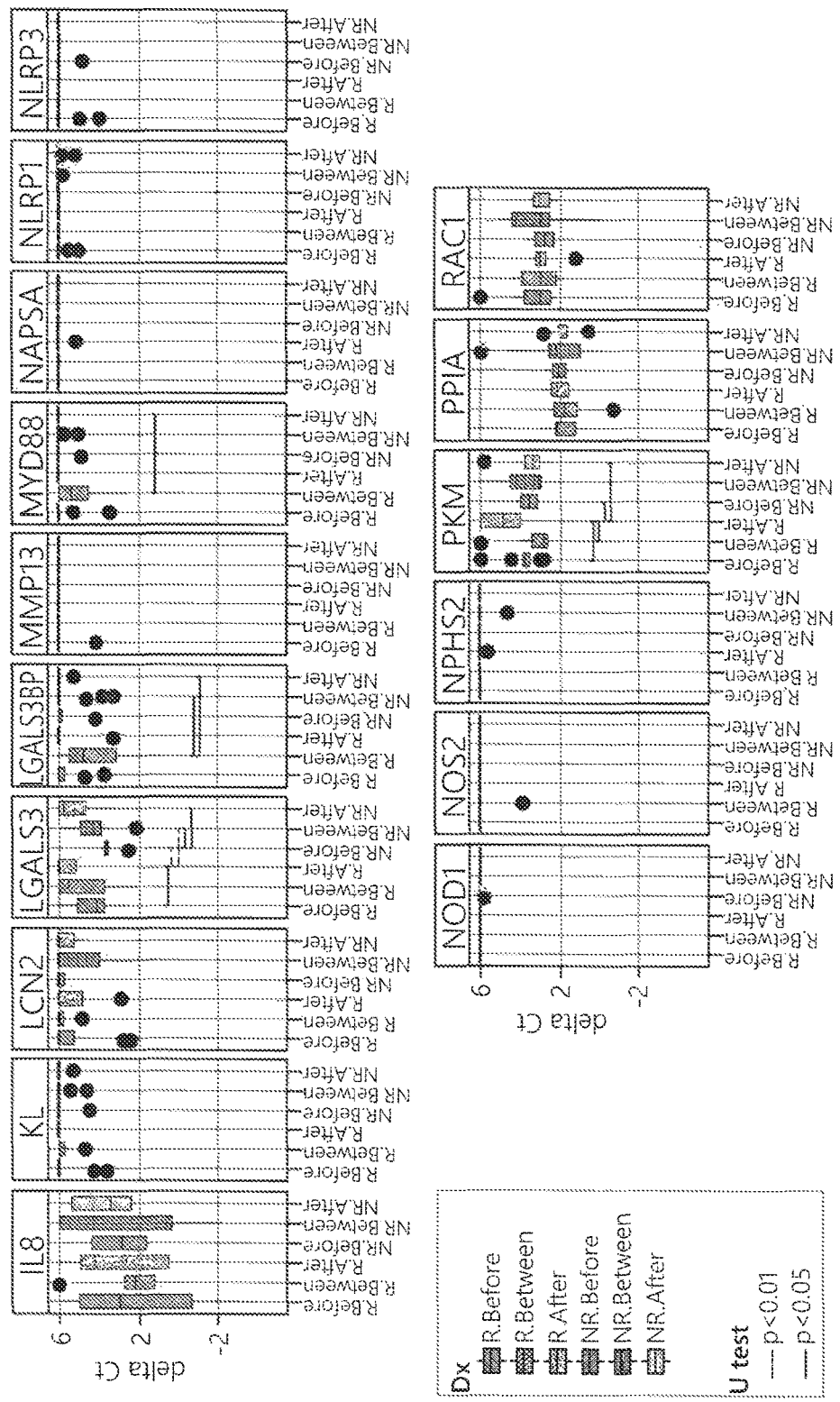
Figure 5D:
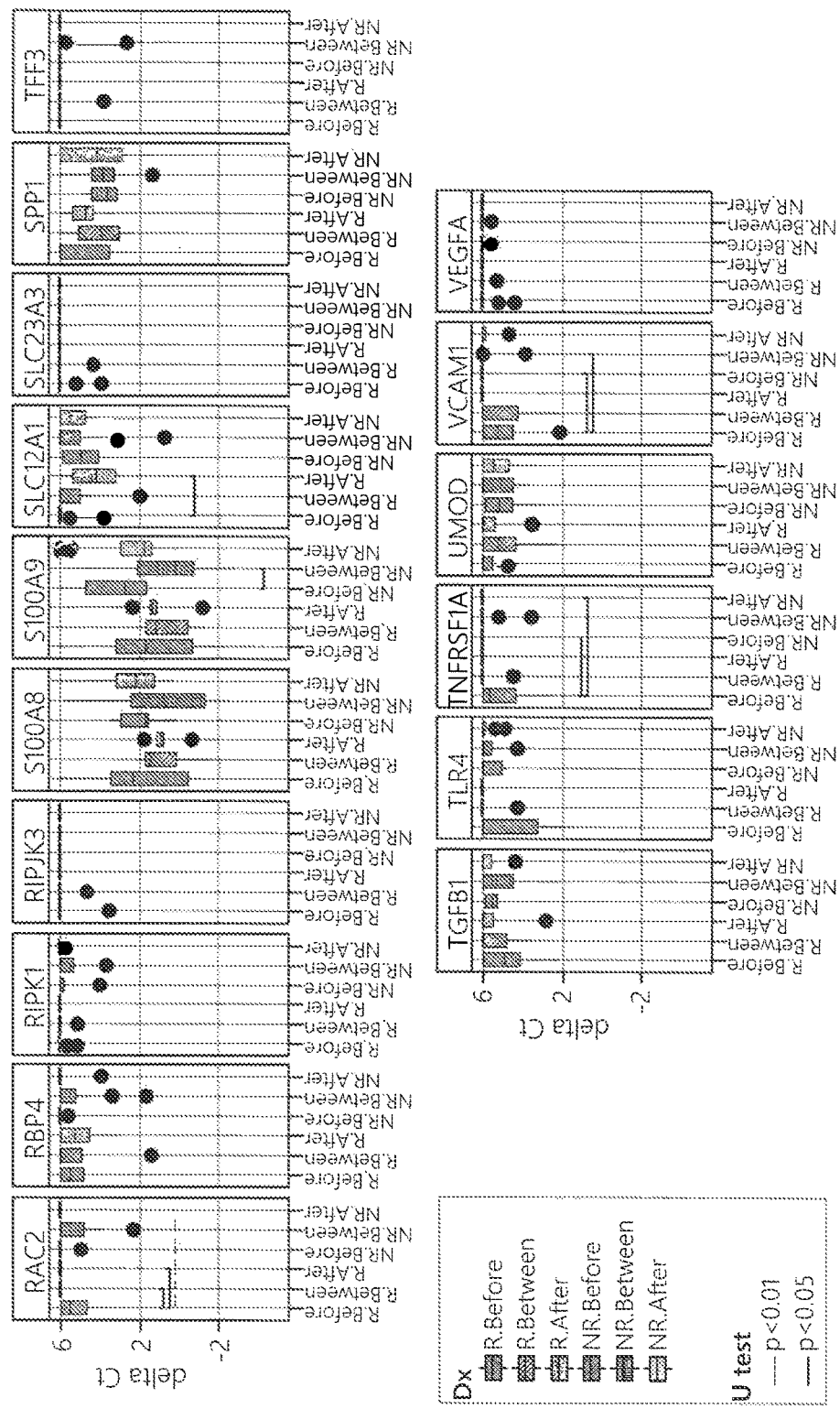
Figure 6B:
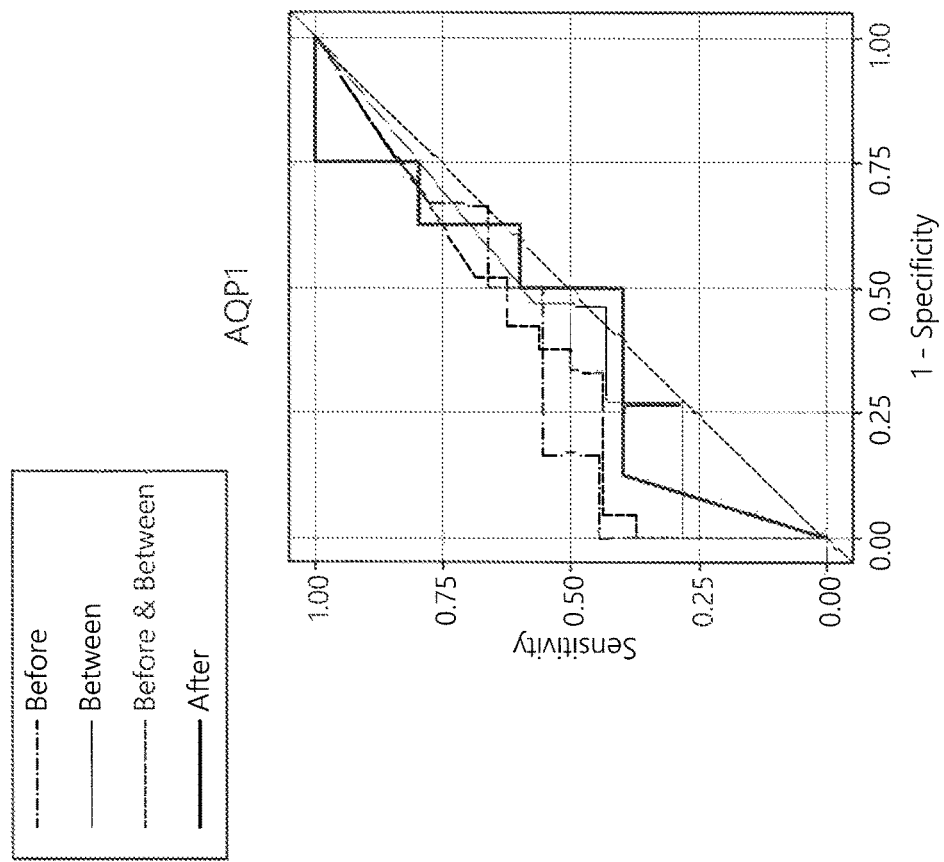
FIG. 6A-6F show ROC curve analysis of AKI recovery markers from urinary EMV.
Figure 6A:
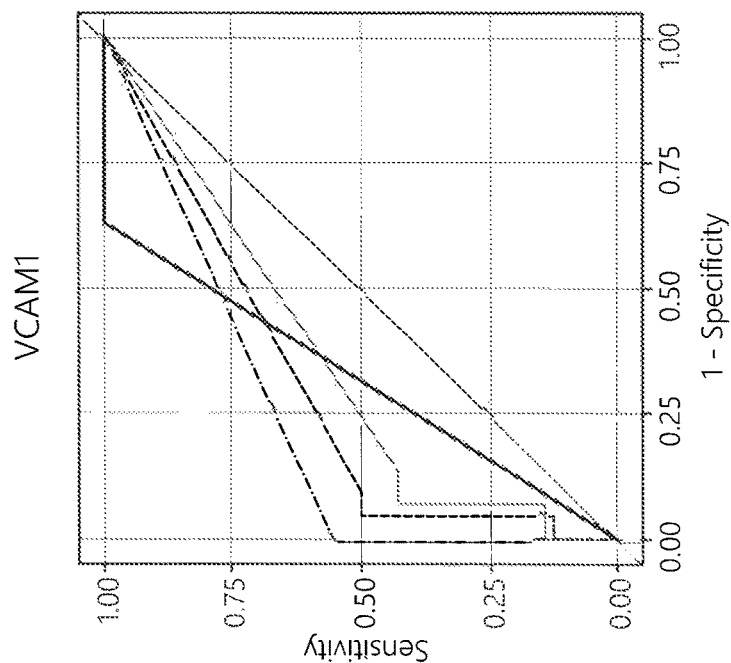
Figure 6D:
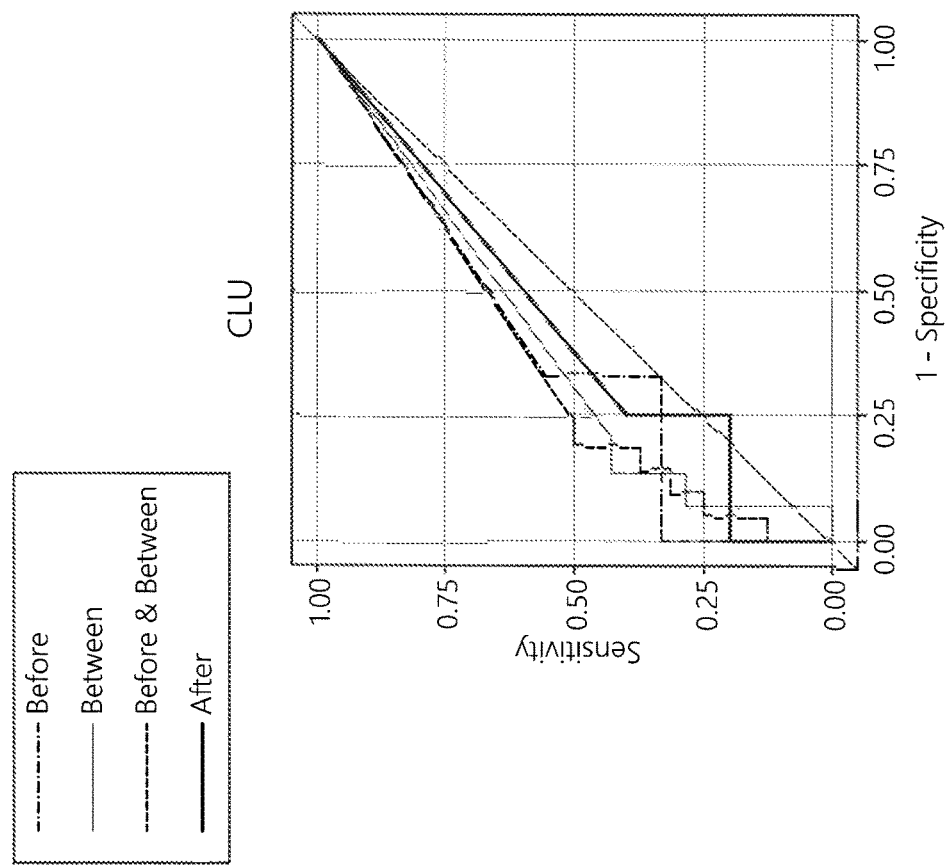
Figure 6C:
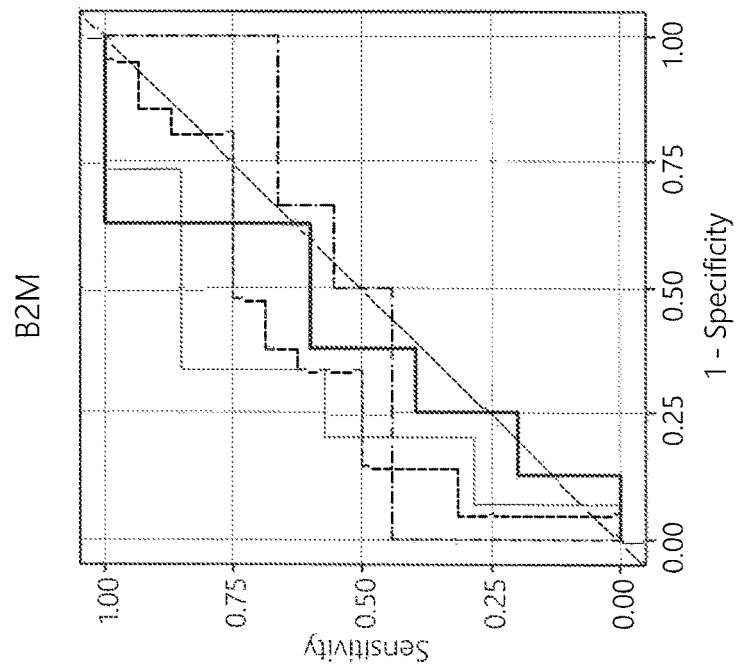
Figure 6F:
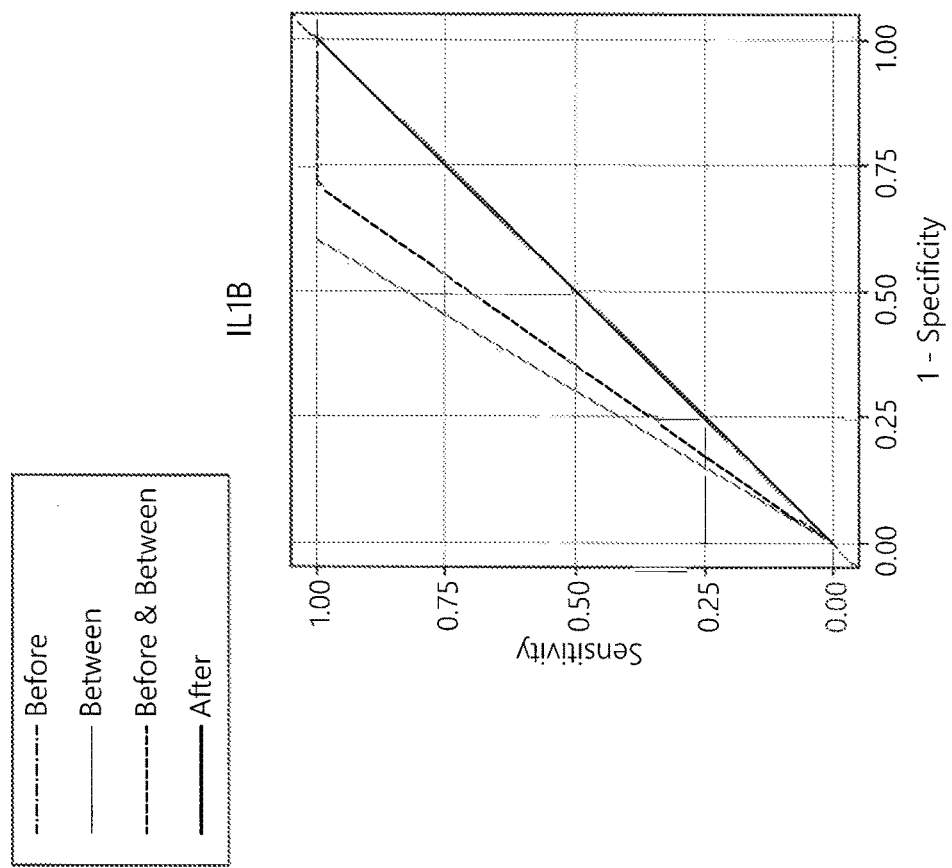
Figure 6E:
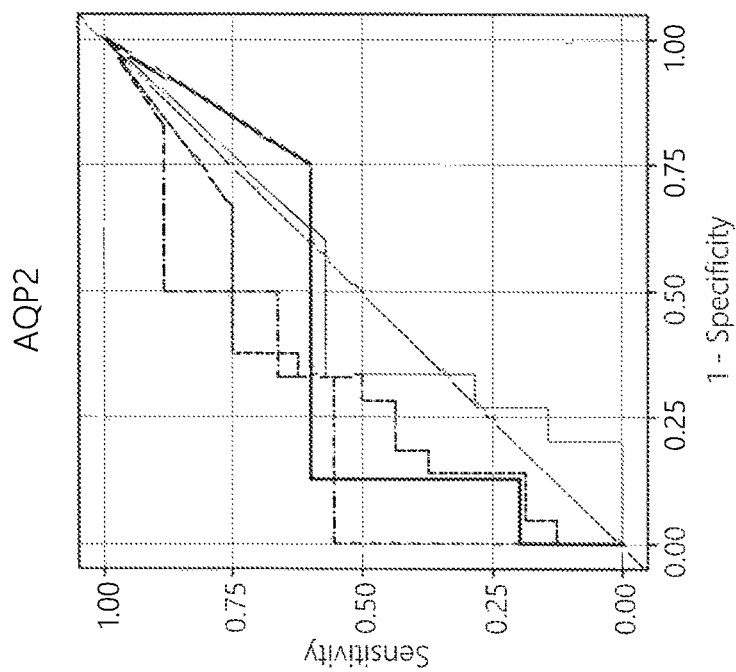
Figure 7B:
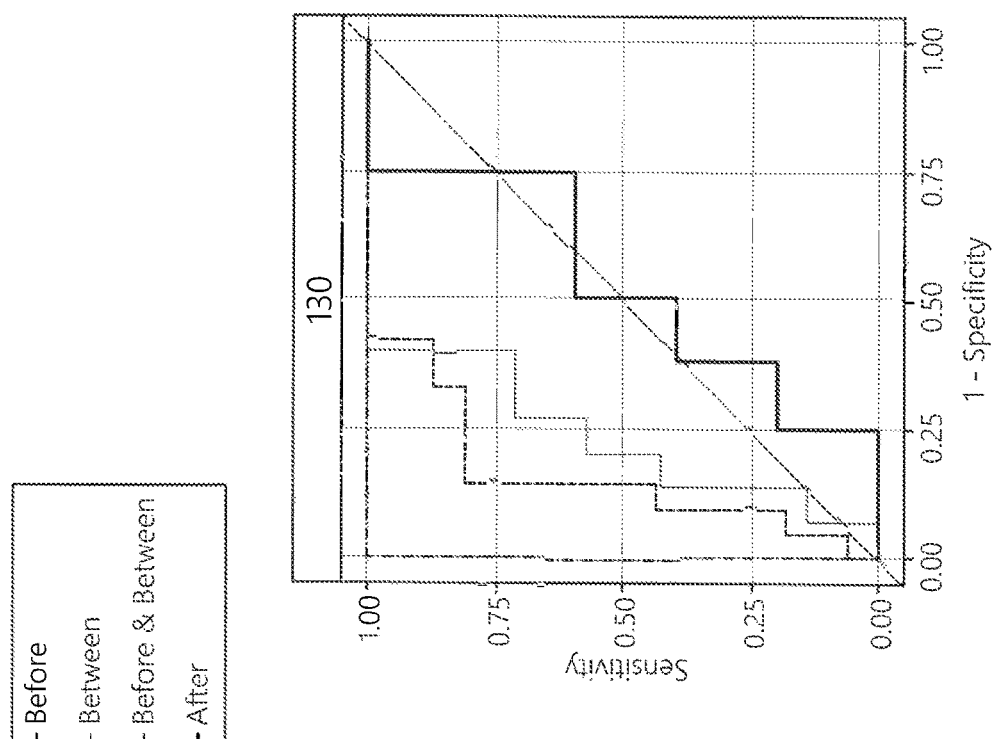
Figure 7A:
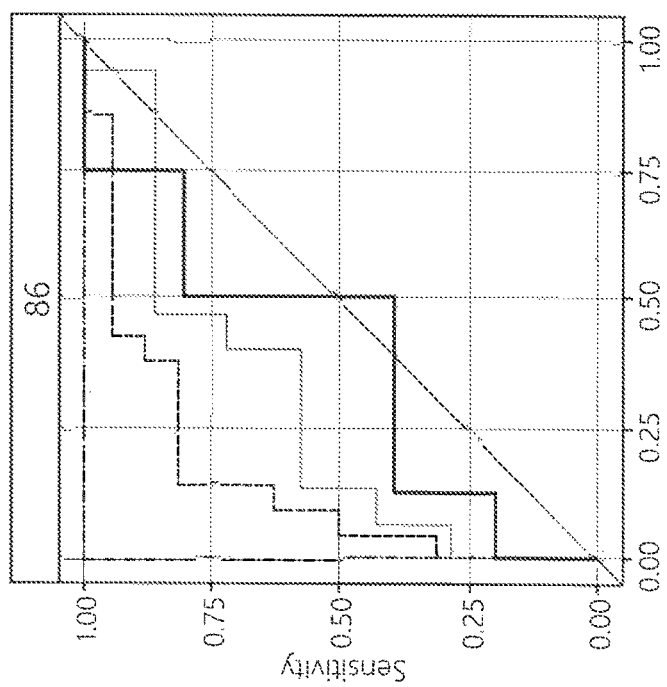
Figures 7C, 7D:
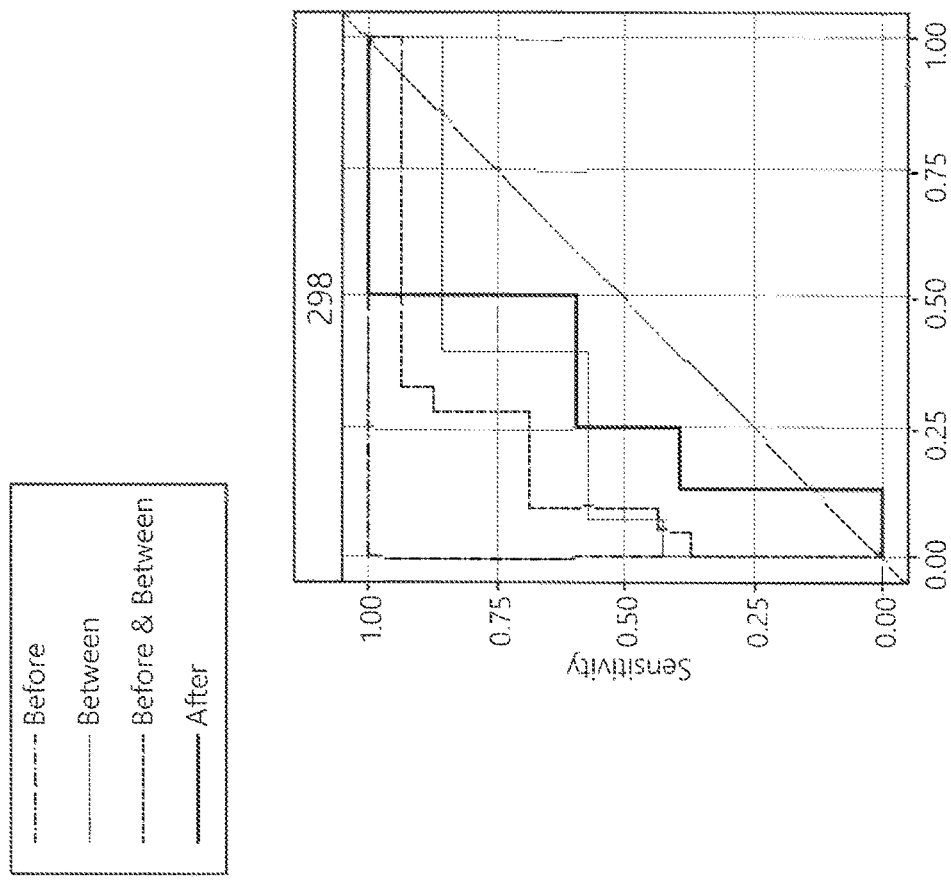
Figure 7H:
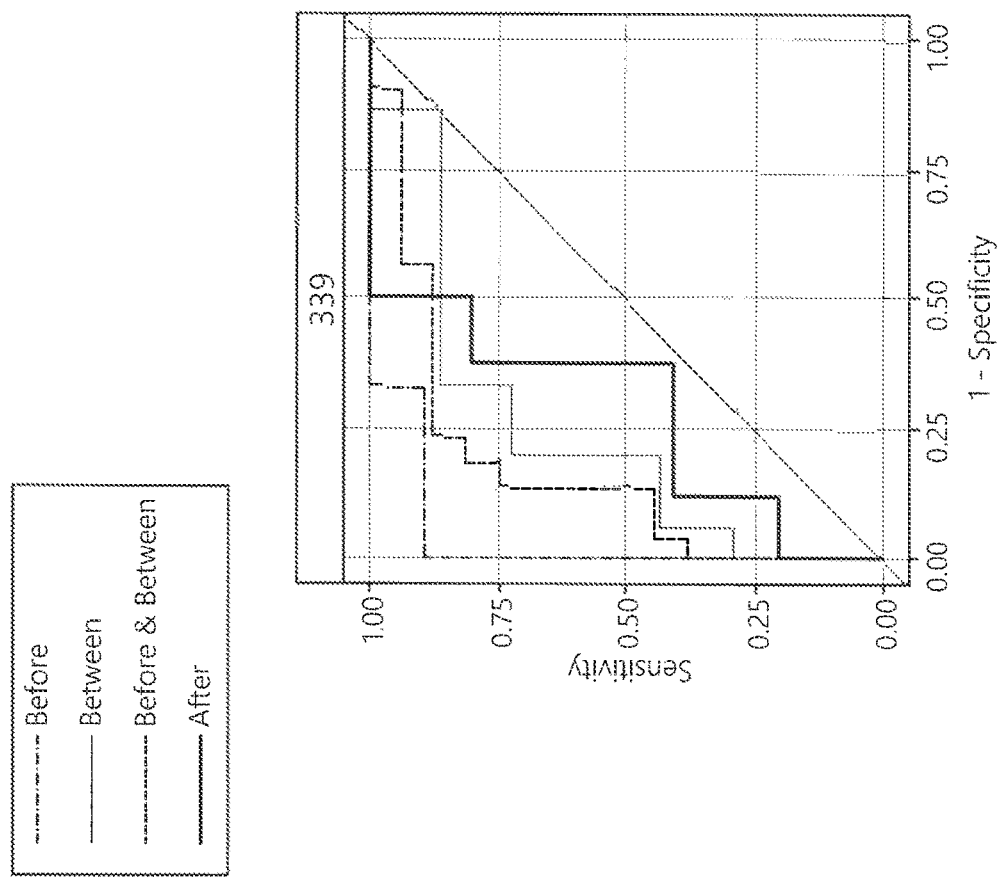
Figure 7G:
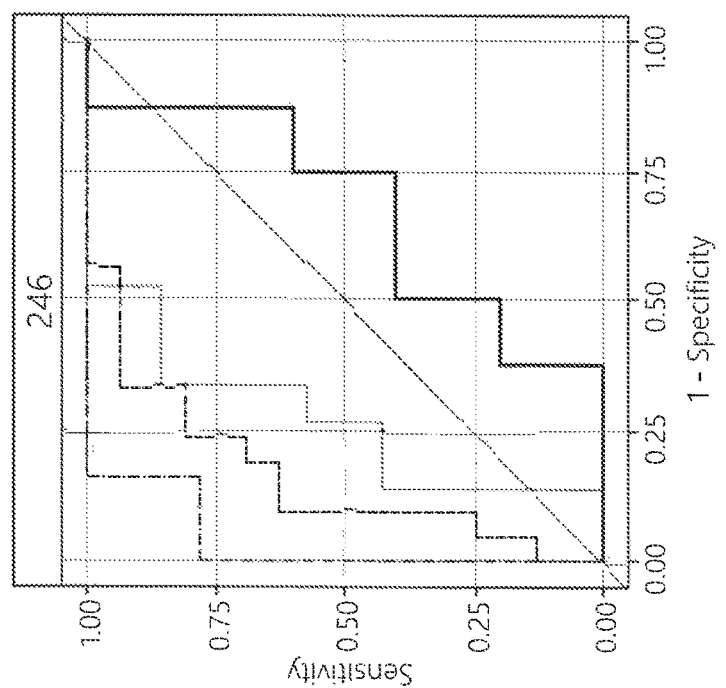
Figure 7J:
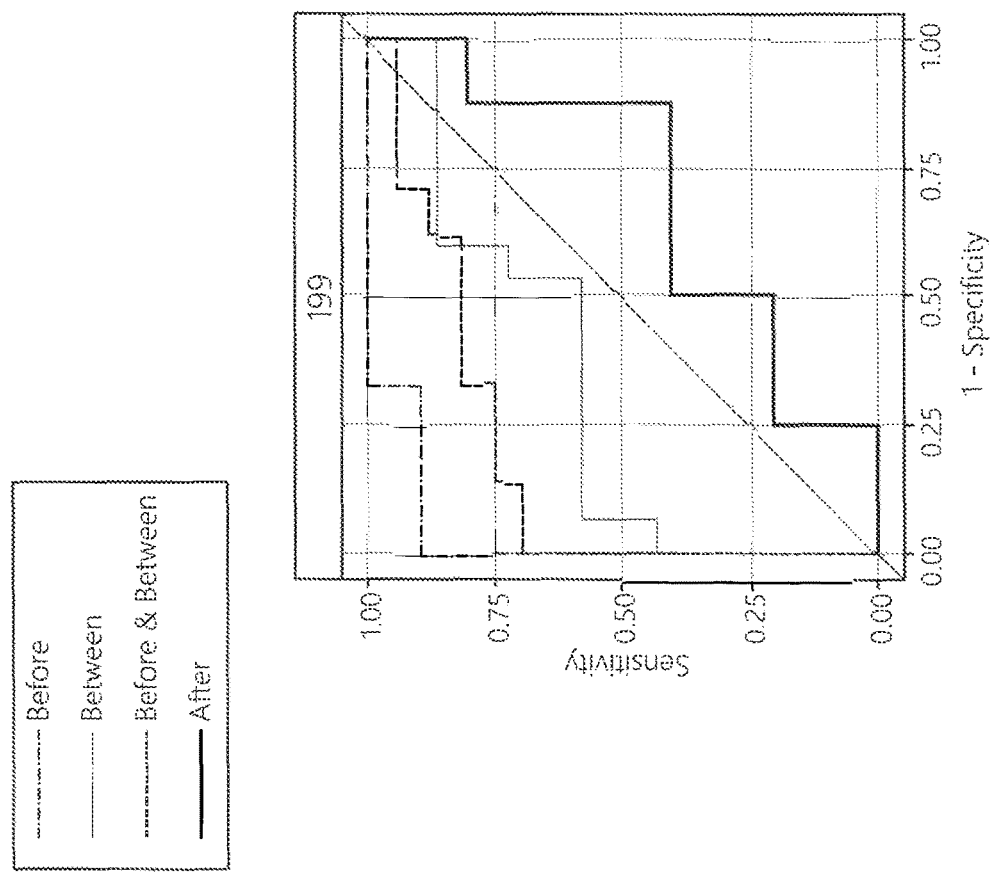
Figure 7I:
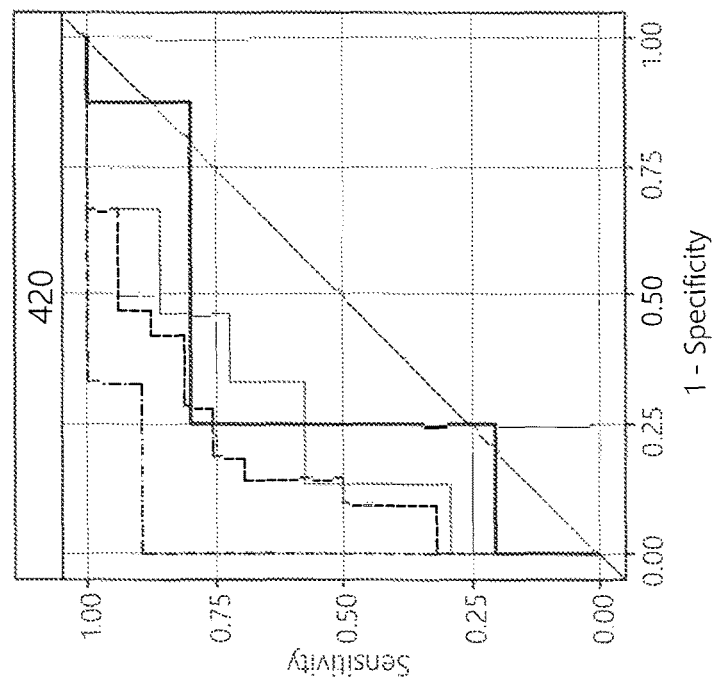

A physician's diagnosis is typically based upon the medical history of the patient as well as current symptoms. In addition to a physical examination that may expose signs of the underlying disease, diagnostic tests may be ordered to confirm an initial diagnosis. Evaluation of kidney function presents a unique situation for diagnostic analysis, as the function of the organ to produce urine, the composition of which results is reflected with concentration changes of compounds in the blood. Thus kidney function can be evaluated using two fluids, urine and/or blood.

Many diagnostic tests are directed to detecting certain proteins in the fluid. However, protein-based assays, while efficient at certain target concentrations, may suffer from lack of sensitivity at low target concentrations. Diagnostic techniques based on nucleic acid detection offer an alternative to protein detection that, in many cases, provides a higher degree of sensitivity. Nucleic acid can be isolated from cells that are obtained from a blood or urine sample, but also exist extracellularly. While several embodiments disclosed herein are directed to the isolation of RNA associated with vesicles present in patient urine samples, in several embodiments, RNA (and the associated markers) that are normally found in blood or plasma are isolated from urine samples. In some embodiments, these blood-borne markers are present in the urine due to damage or disease of the kidney that has compromised the normal blood filtering function of the kidney.

Loss of kidney function is progressive in nature and some markers of loss of function or disease may not be detected by traditional diagnostic methods until the disease is well-established. In such cases, as the kidney disease progresses, the prognosis becomes increasingly poor. As such, early detection of the kidney disease may lead to easier treatment regimes and possibly a significantly improved patient outcome. Thus, there is a need for a more sensitive alternative to the diagnostic tests currently used in the detection and characterization of the early stages of kidney diseases or loss of function.

Vesicle-Associated RNA

Recent studies have demonstrated that a variety of cells release EMV into nearby biological fluids, such as blood, urine, saliva, breast milk. During the exocytotic process, various proteins, mRNA, and miRNA are included in the EMV. Although naked mRNAs are instantly digested and become undetectable due to the presence of endogenous ribonucleases, mRNAs exist stably in EMV by encapsulation within the EMV membranes. Various mRNAs in EMV extracted from plasma and urine have been quantified by RT-qPCR.

EMV are nm-sized particles that contain proteins and nucleic acids such as miRNA and mRNA that are representative of the cells from which the EMV are derived. For example, nucleic acids can be associated with one or more different types of membrane particles (ranging in size from 50-80 nm), exosomes (ranging in size from 50-100 nm), exosome-like vesicles (ranging in size from 20-50 nm), and microvesicles (ranging in size from 100-1000 nm). In several embodiments, these vesicles are isolated and/or concentrated, thereby preserving vesicle associated RNA even if there is a high RNAse extracellular environment. The RNAs within these particles have been shown to be functional and can confer specific activity to target cells.

Exosomes and microvesicles originating from renal tissue can be isolated from urine samples from subjects having normal and diseased conditions. The miRNA and protein profiles from exosomes of subjects diagnosed with AKI are significantly different than those derived from non-AKI subjects. Thus, as described in several embodiments herein, exosomes and microvesicles and their contents can be used as diagnostic markers for screening, detecting and/or monitoring (or other treatment) of AKI.

In several embodiments, there are provided methods for identifying novel diagnostic biomarkers by correlating exosome and microvesicle mRNA expression profiles in urines of hospitalized patients having different known physiological and pathophysiological settings. In some embodiments, new diagnostic biomarkers are a single gene. In other embodiments, new diagnostic biomarkers are a profile of multiple genes. New biomarker profiles may allow diagnosis of organ dysfunction before injury becomes pronounced. In some embodiments, new diagnostic biomarkers aid disease treatment by enabling earlier detection or more accurate prediction of outcomes. Alternatively or in addition, biomarker profiles may guide clinical decision-making regarding treatment regimens. Use of biomarkers present in body fluids such as urine minimizes invasiveness of diagnostic procedures and may increase patient compliance with monitoring. Biomarkers such as neutrophil gelatinase-associated lipocalin (NGAL) or Kidney Injury Molecule-1 (KIM-1) are limited in defining underlying injury mechanisms. Thus a need exists to discover new AKI biomarkers that better define the underlying pathways contributing to kidney damage, better predict outcomes, and better guide selection of treatment regimen.

Figure 8:
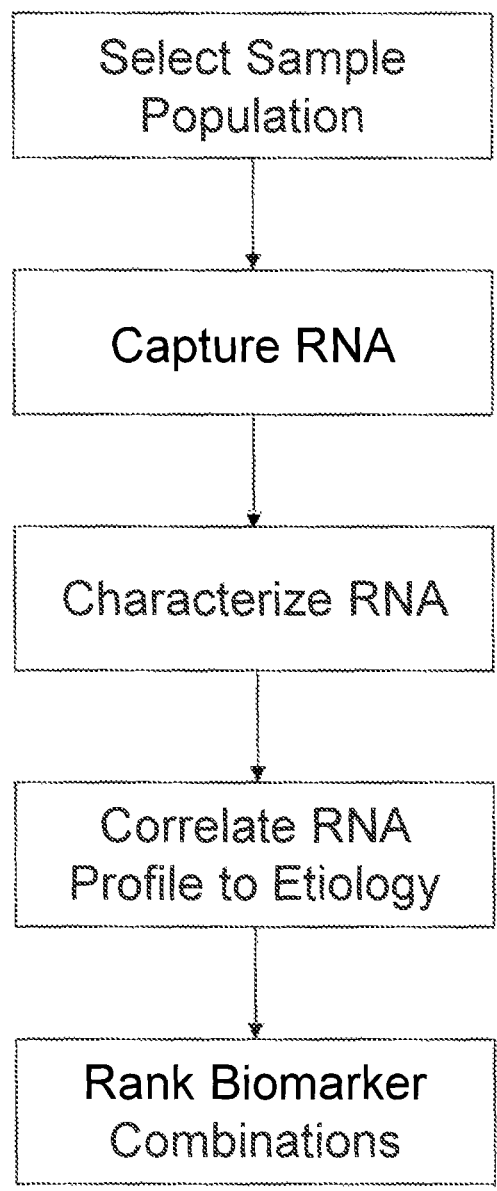
FIG. 8 is a flowchart representation of an embodiment of the method of identifying novel diagnostic biomarkers.

FIG. 8 is a flowchart representation of an embodiment of the method of identifying novel diagnostic biomarkers. As depicted at the top of the flowchart in FIG. 8, some embodiments of the method of identifying novel diagnostic biomarkers includes the step of selecting a sample population of patients displaying different known AKI settings. In several embodiments, the analyses described herein are applicable to human patients, while in some embodiments, the methods are applicable to animals (e.g., veterinary diagnoses).

In at least one embodiment, the sample population of patients includes patients displaying AKI settings selected from the group consisting of healthy donor without AKI, donor having liver disease without AKI, donor having liver disease with AKI, donor having liver disease and chronic kidney disease, donor having undergone cardiac surgery without AKI, and donor having undergone cardiac surgery with AKI. In at least one embodiment, the sample population includes at least one patient from each of the aforementioned AKI settings. In some embodiments, the sample population of patients includes a total of about 10 to 2000 members, about 20 to 1000 members, about 30 to 500 members, or about 50 to 200 members.

Referring back to FIG. 8, some embodiments of the method of identifying novel diagnostic biomarkers includes the step of capturing RNA from a body-fluid sample of each member of the sample population. In some embodiments, mRNA is obtained from exosomes or microvesicles isolated from urines of the sample population. In several embodiments disclosed herein, there are provided methods for the capture of RNA from a sample of patient body fluid and subsequent analysis of that RNA for disease and/or tissue specific markers. In several embodiments, the method comprises isolation of vesicles associated with RNA from a patient urine sample. In other embodiments, vesicles are obtained from plasma, serum, cerebrospinal fluid, sputum, saliva, mucus, tears etc. Many diagnostic tests are designed around using a small patient fluid sample, and in some embodiments, a small amount (e.g. 15-50 mL of urine) is used. However, several embodiments are particularly advantageous because large volumes of patient urine are readily available. Moreover, exosomes found in the urine likely originate from kidney tissue, while the organ source of blood-borne exosomes is less clear.

In several embodiments, the method of identifying novel diagnostic biomarkers further comprises the step of characterizing the RNA captured from body-fluid samples of sample population members. In some embodiments, microvesicle mRNA is quantified by a method selected from the group consisting of reverse-transcription polymerase chain reaction (RT-PCR), real-time RT-PCR, northern blotting, fluorescence activated cell sorting, ELISA, and mass spectrometry. In at least one embodiment, the quantifying comprises amplifying the RNA using RT-PCR. In several embodiments, the RNA comprises poly(A)+ RNA. In some embodiments, the mRNA profile of the body-fluid sample is quantified using qPCR. In at least one embodiment, the mRNA profile is characterized using qPCR to quantify the expression level of a number of target genes. In at least one embodiment, the mRNA profile is characterized by using qPCR to quantify the expression level of a single target gene. In several embodiments, mRNA quantification by qPCR is normalized to GAPDH levels. In some embodiments, the step of characterizing the RNA includes quantifying the expression of 1 to 1000 genes, of 1 to 500 genes, of 1 to 200 genes, of 1 to 100 genes, of 1 to 50 genes, or of 1 to 20 genes.

In several embodiments, the method of identifying novel diagnostic biomarkers further comprises the step of correlating RNA profiles of the body-fluid samples from the source members of the sample population to the physiological or pathophysiological setting displayed by the respective source member of the sample population. In some embodiments, the correlation is performed using statistical analysis. In at least one embodiment, classification formula of target gene combinations are developed using a Mann-Whitney-Wilcoxon test followed by logistic regression analysis to generate ROC for combinations of 1 to 7 genes and using cross-validation to calculate AUC for each ROC. In some embodiments, ROC are generated for 1 to 10 genes, for 1 to 20 genes, for 1 to 50 genes, or for 1 to 100 genes.

In several embodiments, the method of identifying novel diagnostic biomarkers further comprises the step of ranking the biomarkers. In some embodiments, AUC are ranked to identify formulae having greater specificity and sensitivity. In at least one embodiment, formulae are generated to identify biomarkers that are useful for predicting recovery from AKI. In some embodiments, formulae are generated to identify biomarkers that are useful for diagnosing AKI. In some embodiments, formulae are generated to identify biomarkers that are useful for diagnosing the underlying causes of AKI.

The present disclosure relates to the use of urine EMV to detect AKI, and/or treat (or monitor ongoing treatment) of a subject with AKI. A variety of methods can be used, according to the embodiments disclosed herein, to efficiently capture and preserve vesicle associated RNA. In several embodiments, centrifugation on a density gradient to fractionate the non-cellular portion of the sample is performed. In some embodiments, density centrifugation is optionally followed by high speed centrifugation to cause vesicle sedimentation or pelleting. As such approaches may be time consuming and may require expensive and specialized equipment in several embodiments, low speed centrifugation can be employed to collect vesicles.

In several embodiments, filtration (alone or in combination with centrifugation) is used to capture vesicles of different sizes. In some embodiments, differential capture of vesicles is made based on the surface expression of protein markers. For example, a filter may be designed to be reactive to a specific surface marker (e.g., filter coupled to an antibody) or specific types of vesicles or vesicles of different origin. In several embodiments, the combination of filtration and centrifugation allows a higher yield or improved purity of vesicles.

In some embodiments, the markers are unique vesicle proteins or peptides. In some embodiments, the severity or identity of a particular IBD is associated with certain vesicle modifications which can be exploited to allow isolation of particular vesicles. Modification may include, but is not limited to addition of lipids, carbohydrates, and other molecules such as acylated, formylated, lipoylated, myristolylated, palmitoylated, alkylated, methylated, isoprenylated, prenylated, amidated, glycosylated, hydroxylated, iodinated, adenylated, phosphorylated, sulfated, and selenoylated, ubiquitinated. In some embodiments, the vesicle markers comprise non-proteins such as lipids, carbohydrates, nucleic acids, RNA, DNA, etc.

In several embodiments, the specific capture of vesicles based on their surface markers also enables a "dip stick" format where each different type of vesicle is captured by dipping probes coated with different capture molecules (e.g., antibodies with different specificities) into a patient sample.

In several embodiments, EMV from urine were captured on an EMV filter collection tube device. In some embodiments the supernatant from a low speed spin can be the starting point for further isolation using conventional ultra-centrifugation or can then be added to an exosome and microvesicle-capture filter device. In some embodiments, after application of the supernatant to the filter device, another low speed spin may be used to concentrate the particles onto the filter and remove the liquid. A lysis buffer may be added to the filter to release RNA. A low speed spin may be used to transfer the lysate from the filter device and in to the wells of an oligo(dT)-coated plate. The mRNA from the sample may be hybridized to the plate and the captured mRNA can be eluted and may be used for further downstream analysis. In several embodiments, after collection of the biological fluid containing membrane particles, cells, exosomes and microvesicles, molecular analysis of DNA, protein, membrane surface antigens, and miRNA can be performed in addition to mRNA analysis.

In some embodiments, EMV mRNA were released from the filter using a lysis buffer and isolated with an oligo(dT)-coupled plate. Depending on the embodiment, various epithelial-, immune/inflammatory-, blood cell-derived-, chemokine-, and miscellaneous mRNAs are evaluated (e.g., levels of expression are assessed, in some cases versus an appropriate control).

Thus, in several embodiments, the methods disclosed herein relate to the analysis of biological fluid for the presence of exosomes and/or microvesicles in order to identify potential biomarkers for the detection, diagnosis, screening or monitoring of AKI. Biological fluids include, but are not limited to blood, urine, saliva, breast milk, intestinal fluid, and the like. Additionally or alternatively, stool samples can be used in some embodiments.

Free extracellular RNA is quickly degraded by nucleases, making it a potentially poor diagnostic marker. As described above, some extracellular RNA is associated with particles or vesicles that can be found in various biological samples, such as urine. This vesicle associated RNA, which includes mRNA, is protected from the degradation processes in the urine. Microvesicles are shed from most cell types and consist of fragments of plasma membrane. Microvesicles contain RNA, mRNA, microRNA, and proteins and mirror the composition of the cell from which they are shed. Exosomes are small microvesicles secreted by a wide range of mammalian cells and are secreted under normal and pathological conditions. These vesicles contain certain proteins and RNA including mRNA and microRNA. Several embodiments evaluate nucleic acids such as small interfering RNA (siRNA), tRNA, and small activating RNA (saRNA), among others.

In several embodiments the RNA isolated from vesicles from the urine of a patient is used as a template to make cDNA, for example through the use of a reverse transcriptase. In several embodiments, cDNA is amplified using the polymerase chain reaction (PCR). In other embodiments, amplification of nucleic acid and RNA may also be achieved by any suitable amplification technique such as nucleic acid based amplification (NASBA) or primer-dependent continuous amplification of nucleic acid, or ligase chain reaction. Other methods may also be used to quantify the nucleic acids, such as for example, including Northern blot analysis, RNAse protection assay, RNA sequencing, RT-PCR, real-time RT-PCR, nucleic acid sequence-based amplification, branched-DNA amplification, ELISA, mass spectrometry, CHIP-sequencing, and DNA or RNA microarray analysis.

In several embodiments, mRNA is quantified by a method entailing cDNA synthesis from mRNA and amplification of cDNA using PCR. In one preferred embodiment, a multi-well filterplate is washed with lysis buffer and wash buffer. A cDNA synthesis buffer is then added to the multi-well filterplate. The multi-well filterplate can be centrifuged. PCR primers are added to a PCR plate, and the cDNA is transferred from the multi-well filterplate to the PCR plate. The PCR plate is centrifuged, and real time PCR is commenced.

An additional embodiment comprises application of specific antisense primers during mRNA hybridization or during cDNA synthesis. It is preferable that the primers be added during mRNA hybridization, so that excess antisense primers may be removed before cDNA synthesis to avoid carryover effects. The oligo(dT) and the specific primer (NNNN) simultaneously prime cDNA synthesis at different locations on the poly-A RNA. The specific primer (NNNN) and oligo(dT) cause the formation of cDNA during amplification. Even when the specific primer-derived cDNA is removed from the GenePlate by heating each well, the amounts of specific cDNA obtained from the heat denaturing process (for example, using TaqMan quantitative PCR) is similar to the amount obtained from an un-heated negative control. This allows the heat denaturing process to be completely eliminated. Moreover, by adding multiple antisense primers for different targets, multiple genes can be amplified from the aliquot of cDNA, and oligo(dT)-derived cDNA in the GenePlate can be stored for future use.

Another additional embodiment involves a device for high-throughput quantification of mRNA from urine. The device includes a multi-well filterplate containing: multiple sample-delivery wells, an exosome-capturing filter (or filter directed to another biological component of interest) underneath the sample-delivery wells, and an mRNA capture zone under the filter, which contains oligo(dT)-immobilized in the wells of the mRNA capture zone. In order to increase the efficiency of exosome collection, several filtration membranes can be layered together.

In some embodiments, amplification comprises conducting real-time quantitative PCR (TaqMan) with exosome-derived RNA and control RNA. In some embodiments, a Taqman assay is employed. The 5' to 3' exonuclease activity of Taq polymerase is employed in a polymerase chain reaction product detection system to generate a specific detectable signal concomitantly with amplification. An oligonucleotide probe, nonextendable at the 3' end, labeled at the 5' end, and designed to hybridize within the target sequence, is introduced into the polymerase chain reaction assay. Annealing of the probe to one of the polymerase chain reaction product strands during the course of amplification generates a substrate suitable for exonuclease activity. During amplification, the 5' to 3' exonuclease activity of Taq polymerase degrades the probe into smaller fragments that can be differentiated from undegraded probe. In other embodiments, the method comprises: (a) providing to a PCR assay containing a sample, at least one labeled oligonucleotide containing a sequence complementary to a region of the target nucleic acid, wherein the labeled oligonucleotide anneals within the target nucleic acid sequence bounded by the oligonucleotide primers of step (b); (b) providing a set of oligonucleotide primers, wherein a first primer contains a sequence complementary to a region in one strand of the target nucleic acid sequence and primes the synthesis of a complementary DNA strand, and a second primer contains a sequence complementary to a region in a second strand of the target nucleic acid sequence and primes the synthesis of a complementary DNA strand; and wherein each oligonucleotide primer is selected to anneal to its complementary template upstream of any labeled oligonucleotide annealed to the same nucleic acid strand; (c) amplifying the target nucleic acid sequence employing a nucleic acid polymerase having 5' to 3' nuclease activity as a template dependent polymerizing agent under conditions which are permissive for PCR cycling steps of (i) annealing of primers and labeled oligonucleotide to a template nucleic acid sequence contained within the target region, and (ii) extending the primer, wherein said nucleic acid polymerase synthesizes a primer extension product while the 5' to 3' nuclease activity of the nucleic acid polymerase simultaneously releases labeled fragments from the annealed duplexes comprising labeled oligonucleotide and its complementary template nucleic acid sequences, thereby creating detectable labeled fragments; and (d) detecting and/or measuring the release of labeled fragments to determine the presence or absence of target sequence in the sample.

In alternative embodiments, a Taqman assay is employed that provides a reaction that results in the cleavage of single-stranded oligonucleotide probes labeled with a light-emitting label wherein the reaction is carried out in the presence of a DNA binding compound that interacts with the label to modify the light emission of the label. The method utilizes the change in light emission of the labeled probe that results from degradation of the probe. The methods are applicable in general to assays that utilize a reaction that results in cleavage of oligonucleotide probes, and in particular, to homogeneous amplification/detection assays where hybridized probe is cleaved concomitant with primer extension. A homogeneous amplification/detection assay is provided which allows the simultaneous detection of the accumulation of amplified target and the sequence-specific detection of the target sequence.

In alternative embodiments, real-time PCR formats may also be employed. One format employs an intercalating dye, such as SYBR Green. This dye provides a strong fluorescent signal on binding double-stranded DNA; this signal enables quantification of the amplified DNA. Although this format does not permit sequence-specific monitoring of amplification, it enables direct quantization of amplified DNA without any labeled probes. Other such fluorescent dyes that may also be employed are SYBR Gold, YO-PRO dyes and Yo Yo dyes.

Another real-time PCR format that may be employed uses reporter probes that hybridize to amplicons to generate a fluorescent signal. The hybridization events either separate the reporter and quencher moieties on the probes or bring them into closer proximity. The probes themselves are not degraded and the reporter fluorescent signal itself is not accumulated in the reaction. The accumulation of products during PCR is monitored by an increase in reporter fluorescent signal when probes hybridize to amplicons. Formats in this category include molecular beacons, dual-hybe probes, Sunrise or Amplifluor, and Scorpion real-time PCR assays.

Another real-time PCR format that may also be employed is the so-called "Policeman" system. In this system, the primer comprises a fluorescent moiety, such as FAM, and a quencher moiety which is capable of quenching fluorescence of the fluorescent moiety, such as TAMRA, which is covalently bound to at least one nucleotide base at the 3' end of the primer. At the 3' end, the primer has at least one mismatched base and thus does not complement the nucleic acid sample at that base or bases. The template nucleic acid sequence is amplified by PCR with a polymerase having 3'-5' exonuclease activity, such as the Pfu enzyme, to produce a PCR product. The mismatched base(s) bound to the quencher moiety are cleaved from the 3' end of the PCR product by 3'-5' exonuclease activity. The fluorescence that results when the mismatched base with the covalently bound quencher moiety is cleaved by the polymerase, thus removing the quenching effect on the fluorescent moiety, is detected and/or quantified at least one time point during PCR. Fluorescence above background indicates the presence of the synthesized nucleic acid sample.

Another additional embodiment involves a fully automated system for performing high throughput quantification of mRNA in urine, including: robots to apply urine samples, hypotonic buffer, and lysis buffer to the device; an automated vacuum aspirator and centrifuge, and automated PCR machinery.

In some embodiments, in order to more accurately quantify the amount of mRNA, quantification is calculated by comparing the amount of mRNA encoding a marker of AKI to a reference value. In some embodiments the reference value will be the amount of mRNA found in healthy non-diseased patients. In other embodiments, the reference value is the expression level of a house-keeping gene. In certain such embodiments, beta-actin, or other appropriate house-keeping gene is used as the reference value. Numerous other house-keeping genes that are well known in the art may also be used as a reference value. In other embodiments, a house keeping gene is used as a correction factor, such that the ultimate comparison is the expression level of marker from a diseased patient as compared to the same marker from a non-diseased (control) sample. In several embodiments, the house keeping gene is a tissue specific gene or marker, such as those discussed above. In still other embodiments, the reference value is zero, such that the quantification of the markers is represented by an absolute number. In several embodiments a ratio comparing the expression of one or more markers from a diseased patient to one or more other markers from a non-diseased person is made. In several embodiments, the comparison to the reference value is performed in real-time, such that it may be possible to make a determination about the sample at an early stage in the expression analysis. For example, if a sample is processed and compared to a reference value in real time, it may be determined that the expression of the marker exceeds the reference value after only a few amplification cycles, rather than requiring a full-length analysis. In several embodiments, this early comparison is particularly valuable, such as when a rapid diagnosis and treatment plan are required (e.g., to treat aggressive cancers or infections prior to possible development of sepsis).

In additional embodiments, the ability to determine the total efficiency of a given sample by using known amounts of spiked standard RNA results from embodiments being dose-independent and sequence-independent. The use of known amounts of control RNA allows PCR measurements to be converted into the quantity of target mRNAs in the original samples.

In certain embodiments, AKI is detected as a statistically significant upregulation or downregulation of expression of one or more marker mRNAs in EMV collected from a urine sample, with statistical significance being measured with standard statistical analyses with $p \leq 0.05$ representing a statistically significant change. In several embodiments, a significant increase in the expression of one or more marker mRNAs is an indication that the individual is suffering from an AKI. In several embodiments, a significant decrease in expression of one or more marker mRNAs is an indication that the individual is suffering from an AKI. In some embodiments, statistical significance is determined by comparing the expression of one or more marker mRNA in EMV obtained from a urine of an individual to the marker mRNA expression levels in a pool of individuals not suffering from AKI, where the mean and variance of the mRNA expression of the pool are determined by analyzing mRNA expression levels in EMV obtained from a urine of the individuals in the pool. In some embodiments, statistical significance is determined by comparing the expression of one or more marker mRNA in EMV obtained from a urine of an individual at a first time point to the expression of one or more marker mRNA in EMV obtained from a urine of an individual at a second time point. In some embodiments, the mean and variance of the mRNA expression of the individual is determined by analyzing samples in at least triplicate at each of the first and second time points.

In several embodiments, a urine sample obtained from an individual can be combined with one or more agents that facilitate capture of EMV on a vesicle-capture device. For example, the EMV-containing urine sample can be combined with a buffer that alters the pH or salt concentration of the sample, thereby facilitating bonding of the EMV with a vesicle capture material (e.g., glass-fiber filter). Additionally or alternatively, the methods disclosed herein may include passing a buffer over a vesicle capture material after EMV have been retained therein to facilitate elution of the EMV from the vesicle capture material.

In certain embodiments, EMV are captured using a device that comprises a loading reservoir reversibly coupled to a tip that houses a vesicle-capture material, with the loading reservoir having a volume capacity that is two to twenty times larger than the volume capacity of the tip. In some embodiments, an EMV-containing sample is loaded into the loading reservoir and drawn through the vesicle-capture material by centrifugation or by applying a pressure differential across the vesicle capture material. In several aspects, the removable tip of the vesicle-capture device is adapted to rest on a frame that holds the removable tip in close proximity to a substrate. In some embodiments, the device comprises a sample multi-well plate that contains a plurality of sample-delivery wells, a EMV-capturing filter underneath the wells, and a substrate underneath the filter which contains immobilized oligo(dT). In some embodiments, the EMV-containing sample is drawn from the sample-delivery wells across the vesicle capture material by centrifugation of the multi-well plate. In certain embodiments, the device also contains a vacuum box adapted to receive the filter plate to create a seal between the plate and the box, such that when vacuum pressure is applied, the EMV-containing sample is drawn from the sample-delivery wells across the vesicle capture material, thereby capturing the EMV and allowing non-EMV components to be removed by washing the filters. In some embodiments, the EMV components are released from the filter by applying lysis buffer to the filter.

In some embodiments, the substrate includes immobilized oligo(dT). In some embodiments, the substrate includes immobilized nucleotide primers. In some embodiments the substrate includes a gene-chip. In some aspects, the frame or plate forms a substantially liquid tight seal with the substrate. In several embodiments, the method comprises loading the EMV-containing sample into the loading reservoir, drawing the sample across the vesicle-capture material, thereby trapping the EMV on or in the vesicle-capture material, detaching the tip from the loading reservoir, placing the tip into the frame, and releasing the EMV from the vesicle-capture material. In some embodiments, releasing the EMV comprises applying lysis buffer to the vesicle-capture material. Further detail regarding the composition of lysis buffers that may be used in several embodiments can be found in U.S. Pat. No. 8,101,344, filed Mar. 15, 2006, which is incorporated in its entirety by reference herein.

In several embodiments, cDNA is synthesized from oligo (dT)-immobilized mRNA. In certain embodiments, cDNA is then amplified using real time PCR with primers specifically designed for amplification of AKI-associated markers. Further details about the PCR reactions used in some embodiments are also found in U.S. Pat. No. 8,101,344.

After the completion of a PCR reaction, the mRNA (as represented by the amount of PCR-amplified cDNA detected) for one or more AKI markers is quantified. In certain embodiments, quantification is calculated by comparing the amount of mRNA encoding one or more AKI markers to a reference value. In several embodiments, the reference value is expression level of a gene that is not induced in AKI, e.g., a house-keeping gene. In certain embodiments, beta-actin is used as the reference value. Numerous other house-keeping genes that are well known in the art may also be used as a reference value. In other embodiments, a house-keeping gene is used as a correction factor, such that the ultimate comparison is the induced or downregulated expression of one or more AKI markers as compared to the same marker from a pool of non-AKI (control) individuals. In still other embodiments, the reference value is zero, such that the quantification of one or more AKI markers is represented by an absolute number.

In several embodiments, the methods described herein are used to monitor an individual's responsiveness to ongoing AKI treatment. In some such embodiments, a first urine sample is obtained from the individual. In some embodiments, the first urine sample is obtained prior to the administration of any AKI treatment to the individual. In other embodiments, the individual has received treatment for AKI in the past, and will again in the future. In some embodiments, a second urine sample is obtained from the individual at a time after the taking of the first sample. In certain embodiments, this time is several hours, though in other embodiments, the time is several weeks, and in some embodiments up to several months. In other embodiments, additional samples are taken serially over the course of several months. In some embodiments, the samples are frozen until expression analysis, which is performed as described above.

Evaluation of expression levels of AKI responsive markers can thus be used to monitor the progress (e.g., efficiency) of an AKI treatment plan that is administered to the individual. In some embodiments, a significant difference in expression of one or more AKI responsive markers between the post-treatment sample and the pre-treatment sample indicates that the treatment therapy is effective. In other embodiments, a lack of a significant difference in expression of one or more AKI responsive markers between the post-treatment sample and the pre-treatment sample indicates that the treatment therapy is not effective.

In some embodiments, a kit is provided for extracting target components from biological fluid samples. In some embodiments, a kit comprises a capture device and additional items useful to carry out methods disclosed herein. In some embodiments, a kit comprises one or more reagents selected from the group consisting of lysis buffers, chaotropic reagents, washing buffers, alcohol, detergent, or combinations thereof. In some embodiments, kit reagents are provided individually or in storage containers. In several embodiments, kit reagents are provided ready-to-use. In some embodiments, kit reagents are provided in the form of stock solutions that are diluted before use. In some embodiments, a kit comprises plastic parts (optionally sterilized or sterilizable) that are useful to carry out methods herein disclosed. In some embodiments, a kit comprises plastic parts selected from the group consisting of racks, centrifuge tubes, vacuum manifolds, and multi-well plates. Instructions for use are also provided, in several embodiments.

Figure 9:
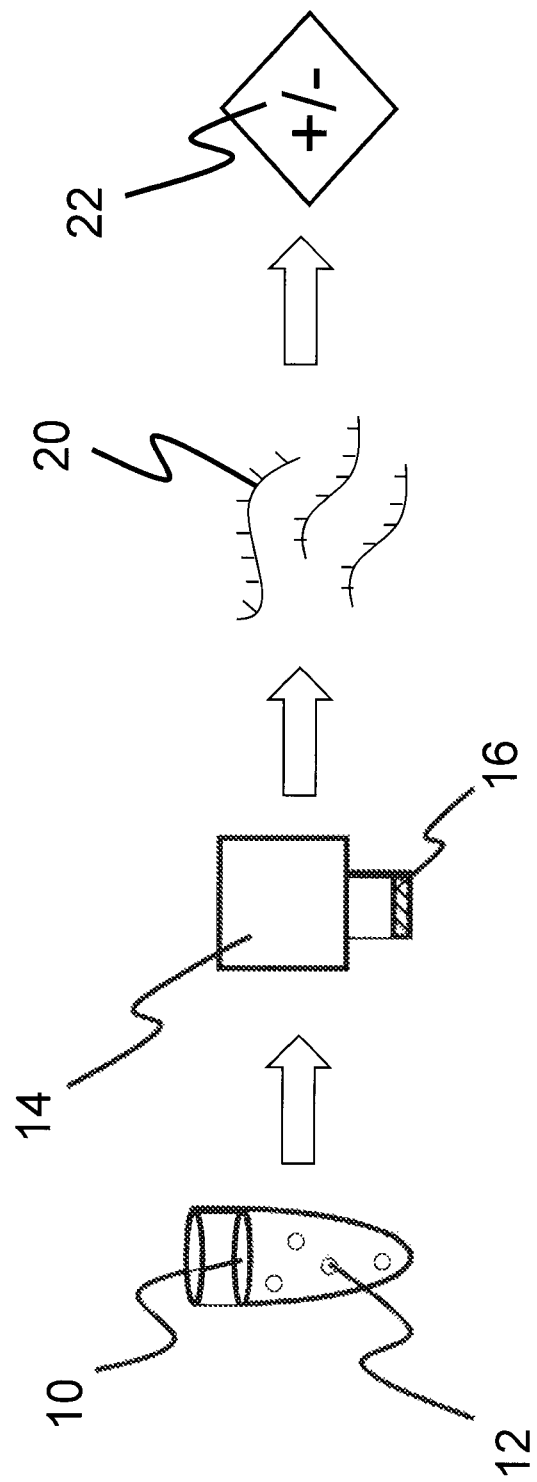
FIG. 9 is a diagrammatic representation of an embodiment of the method of using novel diagnostic biomarkers to treat disease.

FIG. 9 is a diagrammatic representation of an embodiment of the method of using novel diagnostic biomarkers to treat disease. In some embodiments of the method, a body-fluid sample 10 containing exosomes 12 is obtained from a patient (not shown). The body-fluid sample 10 is transferred to an exosome capture device 14, and exosomes 12 are retained in a filter 16 while the rest of the body-fluid sample 10 passes through the capture device 14. The filter 16 is processed to recover RNA 20 that was associated with exosomes 12. The RNA 20 is processed to identify the expression levels of the novel diagnostic biomarkers. The biomarker expression levels of the patient's body-fluid sample 10 are compared to a data table 22 to inform a clinician regarding the diagnosis or treatment of the patient.

In several embodiments, the RNA 20 is processed to identify the expression of the novel diagnostic biomarkers selected from the group consisting of CALM1, AQP2, and SPP1. In some embodiments, the RNA 20 is processed to identify the expression of novel diagnostic biomarkers selected from the group consisting of CALM1, AQP2, and SPP1 to treat AKI. In some embodiments, the RNA 20 is processed to identify the expression of novel diagnostic biomarkers selected from the group consisting of CALM1, AQP2, and SPP1 to diagnose AKI. In some embodiments, the RNA 20 is processed to identify the expression of novel diagnostic biomarkers selected from the group consisting of CALM1, AQP2, and SPP1 to identify the underlying cause or causes of AKI.

Implementation Mechanisms

According to some embodiments, the methods described herein can be implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, server computer systems, portable computer systems, handheld devices, networking devices or any other device or combination of devices that incorporate hard-wired and/or program logic to implement the techniques.

Computing device(s) are generally controlled and coordinated by operating system software, such as iOS, Android, Chrome OS, Windows XP, Windows Vista, Windows 7, Windows 8, Windows Server, Windows CE, Unix, Linux, SunOS, Solaris, iOS, Blackberry OS, VxWorks, or other compatible operating systems. In other embodiments, the computing device may be controlled by a proprietary operating system. Conventional operating systems control and schedule computer processes for execution, perform memory management, provide file system, networking, I/O services, and provide a user interface functionality, such as a graphical user interface ("GUI"), among other things.

In some embodiments, the computer system includes a bus or other communication mechanism for communicating information, and a hardware processor, or multiple processors, coupled with the bus for processing information. Hardware processor(s) may be, for example, one or more general purpose microprocessors.

In some embodiments, the computer system may also include a main memory, such as a random access memory (RAM), cache and/or other dynamic storage devices, coupled to a bus for storing information and instructions to be executed by a processor. Main memory also may be used for storing temporary variables or other intermediate information during execution of instructions to be executed by the processor. Such instructions, when stored in storage media accessible to the processor, render the computer system into a special-purpose machine that is customized to perform the operations specified in the instructions.

In some embodiments, the computer system further includes a read only memory (ROM) or other static storage device coupled to bus for storing static information and instructions for the processor. A storage device, such as a magnetic disk, optical disk, or USB thumb drive (Flash drive), etc., may be provided and coupled to the bus for storing information and instructions.

In some embodiments, the computer system may be coupled via a bus to a display, such as a cathode ray tube (CRT) or LCD display (or touch screen), for displaying information to a computer user. An input device, including alphanumeric and other keys, is coupled to the bus for communicating information and command selections to the processor. Another type of user input device is cursor control, such as a mouse, a trackball, or cursor direction keys for communicating direction information and command selections to the processor and for controlling cursor movement on display. This input device typically has two degrees of freedom in two axes, a first axis (e.g., x) and a second axis (e.g., y), that allows the device to specify positions in a plane. In some embodiments, the same direction information and command selections as cursor control may be implemented via receiving touches on a touch screen without a cursor.

In some embodiments, the computing system may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "module," as used herein, refers to logic embodied in hardware or firmware, or to a collection of software instructions, possibly having entry and exit points, written in a programming language, such as, for example, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules or computing device functionality described herein are preferably implemented as software modules, but may be represented in hardware or firmware. Generally, the modules described herein refer to logical modules that may be combined with other modules or divided into sub-modules despite their physical organization or storage.

In some embodiments, a computer system may implement the methods described herein using customized hard-wired logic, one or more ASICs or FPGAs, firmware and/or program logic which in combination with the computer system causes or programs the computer system to be a special-purpose machine. According to one embodiment, the methods herein are performed by the computer system in response to hardware processor(s) executing one or more sequences of one or more instructions contained in main memory. Such instructions may be read into main memory from another storage medium, such as a storage device. Execution of the sequences of instructions contained in main memory causes processor(s) to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, or other types of storage devices. Volatile media includes dynamic memory, such as a main memory. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between nontransitory media. For example, transmission media includes coaxial cables, copper wire and fiber optics, including the wires that comprise a bus. Transmission media can also take the form of acoustic or light waves, such as those generated during radio-wave and infra-red data communications.

Various forms of media may be involved in carrying one or more sequences of one or more instructions to a processor for execution. For example, the instructions may initially be carried on a magnetic disk or solid state drive of a remote computer. The remote computer can load the instructions into its dynamic memory and send the instructions over a telephone line using a modem or other network interface, such as a WAN or LAN interface. A modem local to a computer system can receive the data on the telephone line and use an infra-red transmitter to convert the data to an infra-red signal. An infra-red detector can receive the data carried in the infra-red signal and appropriate circuitry can place the data on a bus. The bus carries the data to the main memory, from which the processor retrieves and executes the instructions. The instructions received by the main memory may retrieve and execute the instructions. The instructions received by the main memory may optionally be stored on a storage device either before or after execution by the processor.

In some embodiments, the computer system may also include a communication interface coupled to a bus. The communication interface may provide a two-way data communication coupling to a network link that is connected to a local network. For example, a communication interface may be an integrated services digital network (ISDN) card, cable modem, satellite modem, or a modem to provide a data communication connection to a corresponding type of telephone line. As another example, a communication interface may be a local area network (LAN) card to provide a data communication connection to a compatible LAN (or WAN component to communicate with a WAN). Wireless links may also be implemented. In any such implementation, a communication interface sends and receives electrical, electromagnetic or optical signals that carry digital data streams representing various types of information.

A network link may typically provide data communication through one or more networks to other data devices. For example, a network link may provide a connection through a local network to a host computer or to data equipment operated by an Internet Service Provider (ISP). The ISP in turn provides data communication services through the world wide packet data communication network now commonly referred to as the "Internet." The local network and Internet both use electrical, electromagnetic or optical signals that carry digital data streams. The signals through the various networks and the signals on the network link and through a communication interface, which carry the digital data to and from the computer system, are example forms of transmission media.

In some embodiments, the computer system can send messages and receive data, including program code, through the network(s), the network link, and the communication interface. In the Internet example, a server might transmit a requested code for an application program through the Internet, ISP, local network, and communication interface.

The received code may be executed by a processor as it is received, and/or stored in a storage device, or other non-volatile storage for later execution.

EXAMPLES

Specific embodiments will be described with reference to the following examples which should be regarded in an illustrative rather than a restrictive sense.

Example 1

Sample Populations

Urine samples were obtained from 63 patients in different clinical settings with and without AKI and 11 healthy controls (Table 1). The patients were recruited with an informed consent from the following three high risk patient groups: patients with cirrhosis (compensated and decompensated with evidence of portal hypertension and ascites), post cardiac surgery and critically ill patients admitted to the ICU. In each category patients were stratified into AKI and no Aki groups based on their course. Patients who developed AKI had urine samples before, between and after AKI. Urine samples were collected and stored at −80° C. until analysis. AKI was defined by KDIGO criteria as elevation of serum creatinine (sCr) of >0.3 mg/dl within 48 h or 50% increase over baseline sCr. Recovery was defined as return of elevated sCr to within 15% of reference.

Example 2

Urinary EMV mRNA Analysis

Urinary EMV mRNA analysis was performed on urine samples from AKI, no AKI, and healthy control groups to determine expression profiles specific to AKI development. Urine samples were centrifuged at 800×g for 15 min to remove large particles such as urinary cells and casts first. Urine supernatants were collected and mixed with ¼ volumes of 25×PBS, pH 7.4. 12.5 mL of mixtures (10 mL urine supernatants) including EMV were applied to exosome collection tube (Hitachi Chemical Diagnostics, Inc. (HCD), Mountain View, Calif.), and centrifuged at 2,000×g for 10 minutes. Eighty μL of Lysis buffer was added to the filter to lyse EMV captured in the filter. The lysates were then transferred to an oligo(dT)-immobilized microplate by centrifugation and incubated at 4° C. overnight for mRNA hybridization. After six washes with Wash buffer, cDNA was synthesized in the same microplate by adding 30 µL of 1× reverse transcription buffer containing 1.25 mM each of dNTPs, 2.7 U/µL MMLV reverse transcriptase and 0.13 U/µL RNasin, and incubated at 37° C. for 2 hours. Real-time PCR was conducted using ABI 7900HT or ViiA7 real-time PCR system (Life Technologies, Carlsbad, Calif.) in a 5 µL reaction contain in 1×SsoAdvanced SYBR Green Supermix and 500 nM each of primer pairs. The temperature profile was 40 cycles of 95° C. for 30 seconds and 65° C. for 1 minute after the initial denaturation of 95° C. for 10 minutes, followed by melting curve analysis. Real-time PCR data was analyzed by the instrument control software and Excel 2007 (Microsoft, Redmond, Wash.) and R (R Foundation). Gene copy number per sample was obtained by converting threshold cycle values to gene copy numbers using reference curves and an estimated mRNA recovery rate, 10%, by the oligo(dT) microplate. Sixty four mRNA were quantified by qPCR and the obtained mRNA data were normalized by GAPDH using the delta Ct method (FIGS. 1A-1D). Statistical significance was determined by Mann-Whitney-Wilcoxon test with p-value<0.05.

Example 3

Statistical Analysis

In order to develop classification formulas to diagnose AKI development and spontaneous recovery from AKI, logistic regression analysis was employed. First, we tested all the possible combinations of 1 to 4 genes (679,120 combinations in total). For each gene combination, the area under the curve (AUC) was calculated through 10 repeats of 10-fold cross validation. The gene combinations were ranked by the mean AUC and the top 500 combinations were selected for larger-scale calculation and mean AUC for each gene combination was obtained through 100 repeats of 10-fold cross validation. The calculation was conducted using R and AUC calculation was done by 'ROCR' package[4].

Example 4

EMV mRNA Markers for AKI Development

Diagnostic performance of AKI development markers was analyzed by ROC curve. EMV mRNA profiles were compared among the following three groups: AKI, no AKI and healthy control. Before, Between, Before & Between, or After sub-groups in the AKI group was compared with the no AKI group and each AUC was determined (Table 2). The identified differentially expressed genes were CALB1, CALM1, CFLAR, EGF, GSTA1, HIF1A, IL18, PKM, PPIA, RIPK1 and SLC12A1 (FIGS. 1A-1D). Among those genes, especially CALM1, CFLAR, GSTA1, HIF1A and SLC12A1 were differentially expressed between AKI and no AKI groups, therefore could be used as biomarkers of AKI development to identify AKI patients among the other patients. The diagnostic performances of these genes were estimated by the area under the curve (AUC) of ROC curves (FIGS. 2A-2F) and summarized in Table 2, showing that these genes are predicative and diagnostic markers of AKI development.

In order to develop gene classifiers to detect AKI development with higher sensitivity and specificity than single genes, logistic regression analysis and ROC curve analysis was employed as described above. Before, Between, Before & Between, or After sub-groups in the AKI group were compared. The top 20 classifiers are summarized in Table 3 with corresponding AUC. Among those, classifiers #13, #290, #56, #225, #102, #266, #418, #9, #39 and #357 in Table 3 showed the best AUC to detect AKI development (Table 3, FIGS. 3A-3J). These classifiers are capable of predicting and diagnosing AKI development.

Example 5

EMV mRNA Markers for AKI Progression

Urinary EMV mRNA expression profiles in AKI patients were further compared among the Before, Between, and After subgroups to discover markers to monitor AKI progression. These sub-groups were determined by the sampling time relative to the time of AKI development. In this comparison, AQP2, CFLAR, CST3, IL1B, LGALS3, MYD88, NLRP3, RAC2 and TNFRSF1A were identified as differentially expressed genes (FIGS. 4A-4D). As AQP2, CST3 and LGALS3 indicated time-course trend, these genes could be used to monitor the AKI progression.

Example 6

EMV mRNA Markers for AKI Recovery

Some of the patients who develop AKI recover spontaneously without medical intervention. To discover markers to detect AKI recovery, urinary EMV mRNA profiles were compared between Recovery and no Recovery sub-groups in the AKI group. Diagnostic performance of AKI recovery markers was analyzed by ROC curve. Recovery group was compared with non-Recovery group in Before, Between, Before & Between, and After sub-groups. Among the 64 genes, ALB, AQP1, APQ2, B2M, CST3, CXCL1, CXCL3, IL1B, LGALS3, LGALS3BP, MYD88, PKM, RAC2, S100A9, SLC12A1, TNFRSF1A and VCAM1 were differentially expressed among the groups therefore these genes are promising biomarkers to detect AKI recovery (FIGS. 5A-5D). Especially, VCAM1, AQP1, B2M, CLU, AQP2 and IL1B were the most promising biomarkers among them as these genes can distinguish the patients who recover spontaneously from AKI from those who do not with high specify and sensitivity (FIGS. 5A-5D). The diagnostic performances of these genes were estimated by the area under the curve (AUC) of ROC curves (FIGS. 6A-6F) and summarized in Table 4, showing that these genes are predicative and diagnostic markers of AKI recovery.

In order to develop gene classifiers to detect AKI recovery with higher sensitivity and specificity than single genes, logistic regression analysis and ROC curve analysis was employed as described above. Recovery group was compared to non-Recovery group in Before, Between, Before & Between, and After sub-groups and AUC was determined. The top 20 classifiers were summarized in Table 5 with corresponding AUC. Among those, classifiers #86, #130, #247, #298, #299, #84, #246, #339, #420 and #199 in Table 5 showed the best AUC to detect AKI recovery (Table 5, FIGS. 7A-7J). These classifiers are capable of predicting and diagnosing AKI recovery.

Various embodiments of the present invention have been described above. Although this invention has been described with reference to these specific embodiments, the descriptions are intended to be illustrative of the invention and are not intended to be limiting. Various modifications and applications may occur to those skilled in the art without departing from the true spirit and scope of the invention as defined in the appended numbered paragraphs.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "treating a subject for a disease or condition" include "instructing the administration of treatment of a subject for a disease or condition."

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments.

Terms, such as, "first", "second", "third", "fourth", "fifth", "sixth", "seventh", "eighth", "ninth", "tenth", or "eleventh" and more, unless specifically stated otherwise, or otherwise understood within the context as used, are generally intended to refer to any order, and not necessarily to an order based on the plain meaning of the corresponding ordinal number. Therefore, terms using ordinal numbers may merely indicate separate individuals and may not necessarily mean the order therebetween. Accordingly, for example, first and second biomarkers used in this application may mean that there are merely two sets of biomarkers. In other words, there may not necessarily be any intention of order between the "first" and "second" sets of data in any aspects.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 nanometers" includes "10 nanometers."

TABLE 1

Summary of urine samples used in this study.

| Group | Total | Spontaneous Recovery | Cardiac surgery study | Liver disease study | ICU study |
|---|---|---|---|---|---|
| AKI | 51 | 29 | 31 | 8 | 12 |
| Before* | 15 | 6 | 15 | 0 | 0 |
| Between | 23 | 15 | 9 | 4 | 10 |
| After* | 13 | 8 | 7 | 4 | 2 |
| No AKI | 34 | — | 14 | 12 | 8 |
| Healthy control | 11 | — | 0 | 0 | 0 |
| Pre operation | 5 | — | 5 | 0 | 0 |
| Total | 101 (63) | 29 (11) | 50 (18) | 20 (20) | 20 (13) |

*Median day when urine samples were collected before or after AKI development was −2.0 (IQR −2.0 to −1.0) or 2.0 (IQR 1.0 to 2.0), respectively.

TABLE 2

Diagnostic performance of AKI development markers.

| Gene | Before | Between | Before & Between | After |
|---|---|---|---|---|
| CALM1 | 0.816 | 0.685 | 0.736 | 0.692 |
| SLC12A1 | 0.693 | 0.668 | 0.678 | 0.598 |
| CFLAR | 0.749 | 0.619 | 0.670 | 0.670 |
| GSTA1 | 0.667 | 0.634 | 0.647 | 0.731 |
| HIF1A | 0.617 | 0.585 | 0.598 | 0.744 |
| ALB | 0.573 | 0.609 | 0.595 | 0.684 |

TABLE 3

Diagnostic performance of AKI development gene classifiers.

| # | Gene classifier | Before | Between | Before & Between | After |
|---|---|---|---|---|---|
| 13 | CALB1 + CALM1 + CFLAR + GAPDH | 0.920 | 0.716 | 0.796 | 0.729 |
| 290 | CALB1 + CALM1 + GAPDH + SLC12A1 | 0.898 | 0.697 | 0.776 | 0.674 |
| 56 | CALB1 + CALM1 + GAPDH + NLRP1 | 0.863 | 0.711 | 0.771 | 0.647 |
| 225 | CALB1 + CALM1 + GAPDH + TFF3 | 0.861 | 0.691 | 0.758 | 0.618 |
| 102 | CALB1 + CALM1 + GAPDH + RBP4 | 0.847 | 0.698 | 0.757 | 0.627 |
| 266 | CALB1 + CALM1 + GAPDH + NAPSA | 0.855 | 0.689 | 0.755 | 0.636 |
| 418 | CALB1 + CALM1 + GAPDH + SLC23A3 | 0.865 | 0.680 | 0.753 | 0.683 |
| 9 | AQP1 + CALB1 + CALM1 + GAPDH | 0.790 | 0.723 | 0.749 | 0.656 |
| 39 | CALM1 + CLU + LGALS3 + RBP4 | 0.816 | 0.706 | 0.749 | 0.505 |
| 357 | CALB1 + CALM1 + CCL5 + GAPDH | 0.820 | 0.692 | 0.742 | 0.622 |
| 451 | CALM1 + DEFA3 + GAPDH + LGALS3 | 0.824 | 0.688 | 0.741 | 0.643 |
| 374 | CALM1 + GAPDH + LGALS3 + RBP4 | 0.812 | 0.696 | 0.741 | 0.577 |
| 240 | CALM1 + CFLAR + GAPDH + RBP4 | 0.802 | 0.702 | 0.741 | 0.699 |

TABLE 3-continued

Diagnostic performance of AKI development gene classifiers.

| # | Gene classifier | Before | Between | Before & Between | After |
|---|---|---|---|---|---|
| 74 | CALB1 + CALM1 + CCL5 + LGALS3 | 0.800 | 0.703 | 0.741 | 0.484 |
| 204 | CALB1 + CALM1 + LGALS3 + RBP4 | 0.820 | 0.687 | 0.739 | 0.439 |
| 73 | AQP2 + CALB1 + CALM1 + GAPDH | 0.788 | 0.699 | 0.735 | 0.719 |
| 79 | CALM1 + CASP1 + GAPDH + S100A8 | 0.767 | 0.711 | 0.733 | 0.704 |
| 99 | C3 + CALM1 + GAPDH + RBP4 | 0.757 | 0.712 | 0.73 | 0.568 |
| 414 | CALM1 + CFLAR + GAPDH + TLR4 | 0.800 | 0.674 | 0.724 | 0.801 |
| 158 | CALB1 + CALM1 + GAPDH + RIPK3 | 0.753 | 0.702 | 0.722 | 0.681 |

TABLE 4

Diagnostic performance of AKI recovery markers.

| Gene | Before | Between | Before & Between | After |
|---|---|---|---|---|
| VCAM1 | 0.778 | 0.657 | 0.708 | 0.688 |
| AQP1 | 0.667 | 0.581 | 0.655 | 0.600 |
| B2M | 0.537 | 0.724 | 0.649 | 0.600 |
| CLU | 0.630 | 0.619 | 0.646 | 0.575 |
| IL1B | 0.500 | 0.700 | 0.643 | 0.500 |
| AQP2 | 0.750 | 0.505 | 0.643 | 0.600 |

TABLE 5

Diagnostic performance of AKI recovery gene classifiers.

| # | Gene classifier | Before | Between | Before & Between | After |
|---|---|---|---|---|---|
| 86 | AQP2 + B2M + GSTP1 + TNFRSF1A | 1.000 | 0.714 | 0.848 | 0.625 |
| 130 | ACTB + AQP1 + RIPK1 + VCAM1 | 1.000 | 0.771 | 0.842 | 0.475 |
| 247 | AQP1 + LGALS3 + RIPK1 + VCAM1 | 1.000 | 0.743 | 0.839 | 0.575 |
| 298 | B2M + GSTP1 + IL1B + TNFRSF1A | 1.000 | 0.733 | 0.836 | 0.700 |
| 299 | B2M + GSTP1 + TNFRSF1A + VCAM1 | 1.000 | 0.714 | 0.821 | 0.725 |
| 84 | AQP1 + CST3 + RIPK1 + VCAM1 | 0.963 | 0.781 | 0.848 | 0.475 |
| 246 | AQP1 + IL10 + RIPK1 + VCAM1 | 0.963 | 0.733 | 0.839 | 0.325 |
| 339 | B2M + HIF1A + TNFRSF1A + VCAM1 | 0.963 | 0.762 | 0.833 | 0.725 |
| 420 | B2M + CXCL3 + TNFRSF1A + VCAM1 | 0.963 | 0.752 | 0.827 | 0.675 |
| 199 | AQP1 + IL1B + UMOD + VCAM1 | 0.963 | 0.686 | 0.824 | 0.300 |
| 39 | AQP1 + RIPK1 + TGFB1 + VCAM1 | 0.944 | 0.771 | 0.851 | 0.425 |
| 197 | AQP1 + CXCL1 + RIPK1 + VCAM1 | 0.944 | 0.762 | 0.842 | 0.525 |
| 288 | AQP1 + B2M + GSTP1 + TNFRSF1A | 0.944 | 0.724 | 0.827 | 0.625 |
| 289 | AQP1 + GSTP1 + IL1B + VCAM1 | 0.926 | 0.733 | 0.836 | 0.25 |
| 162 | AQP1 + GSTP1 + RIPK1 + VCAM1 | 0.926 | 0.743 | 0.830 | 0.475 |
| 245 | AQP1 + HIF1A + RIPK1 + VCAM1 | 0.926 | 0.771 | 0.824 | 0.500 |
| 63 | AQP1 + B2M + RIPK1 + VCAM1 | 0.889 | 0.857 | 0.869 | 0.475 |
| 64 | AQP1 + CASP1 + RIPK1 + VCAM1 | 0.889 | 0.848 | 0.854 | 0.375 |
| 65 | AQP2 + B2M + GSTP1 + RIPK1 | 0.889 | 0.848 | 0.851 | 0.625 |
| 172 | B2M + RIPK1 + TNFRSF1A + VCAM1 | 0.889 | 0.800 | 0.836 | 0.700 |

What is claimed is:

1. A method of treating an acute kidney injury (AKI) in a human subject, the method comprising:
   (A) having a vesicle-containing sample obtained from said human subject sent to a laboratory for the laboratory to perform an assay comprising the following steps (1)-(3):
      (1) capturing at least a portion of vesicles from said sample on or in a vesicle-capture material, thereby generating a vesicle sample;
      (2) quantifying an expression level of at least one gene in said vesicle sample, wherein said at least one gene comprises CALM1 and at least one additional gene selected from the group consisting of SLC12A1, CFLAR, GSTA1, HIF1A, and ALB;
      (3) determining that said subject has said AKI due to said expression level of each of said at least one gene being significantly different from the expression level of the respective gene in a vesicle sample of a healthy human control subject not suffering from said AKI, thereby diagnosing said subject as having AKI; and
   (B) administering an effective amount of an AKI medication to the human subject having said AKI, wherein said AKI medication is selected from the group consisting of a diuretic agent, an intravenous fluid, a steroid medication, a plasma exchange, and a cyclophosphamide, thereby treating said AKI in said human subject.

2. The method of claim 1, wherein said vesicle-containing sample is a urine sample.

3. The method of claim 1, wherein capturing comprises passing said vesicle-containing sample through a filter comprising glass fiber.

4. The method of claim 1, further comprising lysing said vesicle sample on or in said vesicle-capture material.

5. The method of claim 1, wherein quantifying an expression level of at least one gene in said vesicle sample comprises quantifying said expression level of three genes.

6. The method of claim 1, wherein capturing further comprises:
  receiving said fluid sample; and
  passing said fluid sample through a vesicle capture material adapted to capture a captured vesicle population within said vesicle capture material.

7. The method of claim 6, wherein quantifying comprises:
  positioning said vesicle capture material and said captured vesicle population adjacent to a substrate comprising immobilized oligo(dT);
  applying lysis buffer to said vesicle capture material, thereby lysing said captured vesicle population;
  hybridizing one or more mRNA from said captured vesicle population to said substrate;
  synthesizing directly on said substrate one or more cDNA from said one or more mRNA; and
  quantifying by PCR analysis of said one or more cDNA an expression level of a marker mRNA in said captured vesicle population.

8. The method of claim 6, wherein receiving comprises receiving said fluid sample from a medical professional.

9. The method of claim 7, wherein said vesicle capture material comprises glass fiber.

10. The method of claim 9, wherein passing comprises loading said fluid sample into a device comprising a loading reservoir removably attached to a tip, wherein said vesicle capture material is housed within said tip.

11. The method of claim 1, wherein determining further comprises:
  determining a gene classifier by summing the expression level of at least two of the at least one genes; and
  determining whether the gene classifier is significantly different from a respective gene classifier in a vesicle sample of a healthy human control subject not suffering from said AKI.

12. The method of claim 11, wherein the gene classifier comprises the expression levels of at least CALB1 and CALM1.

13. The method of claim 12, wherein the gene classifier further comprises the expression level of GAPDH.

* * * * *